(12) United States Patent
Packham et al.

(10) Patent No.: US 8,247,372 B2
(45) Date of Patent: Aug. 21, 2012

(54) DEPSIPEPTIDES AND THEIR THERAPEUTIC USE

(75) Inventors: Graham Keith Packham, Wiltshire (GB); Arasu Ganesan, Hampshire (GB); Alexander Richard Liam Cecil, Hampshire (GB)

(73) Assignee: University of Southampton, Hampshire (GB)

( * ) Notice: Subject to any disclaimer, the term of this patent is extended or adjusted under 35 U.S.C. 154(b) by 353 days.

(21) Appl. No.: 12/515,880

(22) PCT Filed: Nov. 23, 2007

(86) PCT No.: PCT/GB2007/050709
§ 371 (c)(1),
(2), (4) Date: May 21, 2009

(87) PCT Pub. No.: WO2008/062232
PCT Pub. Date: May 29, 2008

(65) Prior Publication Data
US 2010/0056434 A1    Mar. 4, 2010

(30) Foreign Application Priority Data
Nov. 23, 2006    (GB) .................................. 0623388.6

(51) Int. Cl.
*A61K 38/12*    (2006.01)
*A61P 37/00*    (2006.01)

(52) U.S. Cl. ...... 514/2.9; 514/21.1; 514/19.4; 514/19.5; 530/317

(58) Field of Classification Search .................. None
See application file for complete search history.

(56) References Cited

U.S. PATENT DOCUMENTS
6,670,326 B1 * 12/2003 Nagai et al. .................. 514/19.3

FOREIGN PATENT DOCUMENTS
| EP | 1 142 905 | 10/2001 |
|---|---|---|
| EP | 1 548 026 | 6/2005 |
| JP | 1 142 905 | * 10/2001 |

OTHER PUBLICATIONS
Yurek-George, 2004, JACS, 126, 1030-1031.*
Miller, 2004, Expert Opin. Ther. Patents, 14, 791-804.*
Yurek-George et al., "Total synthesis of spiruchostatin A, a potent histone deacetylase inhibitor", *Journal of the American Chemical Society*, vol. 126, No. 4, pp. 1030-1031, 2004.

* cited by examiner

*Primary Examiner* — Karlheinz R Skowronek
*Assistant Examiner* — Satyanarayana R Gudibande
(74) *Attorney, Agent, or Firm* — Saliwanchik, Lloyd & Eisenschenk

(57) ABSTRACT

Compounds which are Spiruchostatin analogues of the general formula (I) or (I'), isosteres thereof and pharmaceutically acceptable salts thereof are found to inhibit HDAC wherein $R_1$, $R_2$, $R_3$ and $R_4$ are the same or different and represent an amino acid side chain moiety and each $R_6$ is the same or different and represents hydrogen or $C_1$-$C_4$ alkyl.

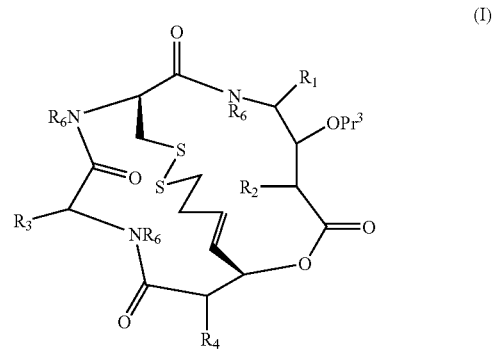

(I)

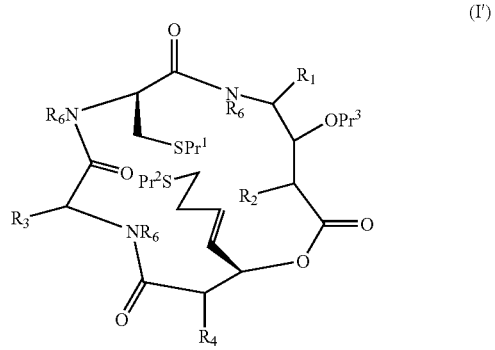

(I')

23 Claims, No Drawings

DEPSIPEPTIDES AND THEIR THERAPEUTIC USE

This application is a National Stage Application of International Application Number PCT/GB2007/050709, filed Nov. 23, 2007; which claims priority to Great Britain Application No. 0623388.6, filed Nov. 23, 2006 by reference in its entirety.

FIELD OF THE INVENTION

The present invention relates to depsipeptides which act as inhibitors of histone deacetylase (HDAC) and therefore have therapeutic utility.

BACKGROUND OF THE INVENTION

Class I and class II HDACs are zinc metalloenzymes that catalyse the hydrolysis of acetylated lysine residues. In histones, this returns lysines to their normal protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

Two natural product depsipeptides, FK228 and Spiruchostatin A, have been reported to have potential as HDAC inhibitors. However, there are limited opportunities to chemically modify or optimize the biological or physicochemical properties of these natural products in order to provide analogues that have the potential for use in treating human diseases.

SUMMARY OF THE INVENTION

It has now surprisingly been found that compounds of the general formulae (I) and (I') act as inhibitors of HDAC. Accordingly, novel compounds of the present invention are Spiruchostatin analogues of formula (I) or (I')

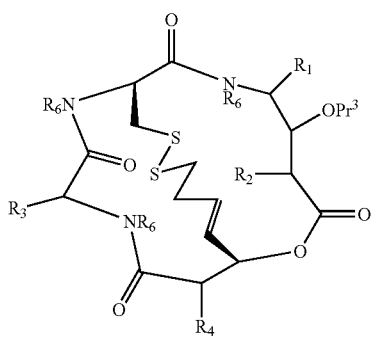

(I)

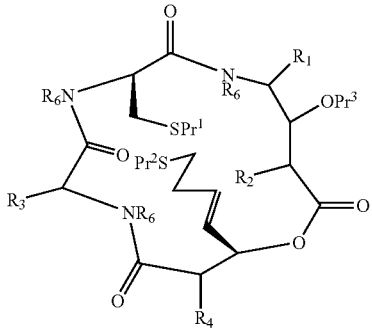

(I')

including isosteres and pharmaceutically acceptable salts thereof, wherein $R_1$ and $R_3$ are the same or different and each represents an amino acid side chain moiety;

$R_2$ and $R_4$ are the same or different and each is selected from —H, —$C_1$-$C_6$ alkyl, —$C_2$-$C_6$ alkenyl, -L-O—C(O)—R', -L-C(O)—O—R", -L-A, -L-NR"R", -L-Het-C(O)-Het-R" and -L-Het-R", wherein L is a $C_1$-$C_6$ alkylene group, A is phenyl or a 5- to 6-membered heteroaryl group, each R' is the same or different and represents $C_1$-$C_4$ alkyl, each R" is the same or different and represents H or $C_1$-$C_6$ alkyl, each -Het- is the same or different and is a heteroatom spacer selected from —O—, —N(R''')- and —S— and each R''' is the same or different and represents H or $C_1$-$C_4$ alkyl.

each $R_6$ is the same or different and represents hydrogen or $C_1$-$C_4$ alkyl;

and $Pr^1$ and $Pr^2$ are the same or different and each represents hydrogen or a protecting group.

The present invention further provides the use of a Spiruchostatin analogue as defined above, in the manufacture of a medicament for use as an inhibitor of HDAC.

DESCRIPTION OF PREFERRED EMBODIMENTS

Synthesis of compounds of formulae I and I' is typically conducted using amino acids of which —CO—CR—NH— forms part of the macrocycle and R is a side-chain moiety. $R_1$ and $R_3$ may be introduced in this way. $R_2$ and $R_4$ may not necessarily be derived from an amino acid.

As used herein, the term "amino acid side chain moiety" refers to any amino acid side chain present in natural and unnatural amino acids. Examples of amino acid side chain moieties derived from unnatural amino acids, with the amino acids from which they are derived shown in brackets, are —$(CH_2)_2$—C(O)—O—C($CH_3)_3$ (tert-butoxycarbonylmethylanaline), —$(CH_2)_4$—NH—C(O)—O—C($CH_3)_3$ (Nε-(tert-butoxycarbonyl)-lysine) and, in particular, —$(CH_2)_3$—NH—C(O)$NH_2$ (citrulline), —$CH_2$—$CH_2$OH (homoserine) and —$(CH_2)_2$—$CH_2NH_2$ (ornithine).

A $C_1$-$C_6$ alkyl group or moiety can be linear or branched. Typically, it is a $C_1$-$C_4$ alkyl group or moiety, for example methyl, ethyl, n-propyl, i-propyl, n-butyl, sec-butyl and t-butyl. Preferred examples include methyl, i-propyl and t-butyl.

A $C_2$-$C_6$ alkenyl group or moiety can be linear or branched. Typically, it is a $C_2$-$C_4$ alkenyl group or moiety. It is preferred that the alkenyl radicals are mono or diunsaturated, more preferably monounsaturated. Examples include vinyl, allyl, 1-propenyl, isopropenyl, 1-butenyl, 2-butenyl and 3-butenyl.

An alkylene group is an alkyl group as defined above which is divalent.

A thiol-protecting group (for $Pr^1$ and $Pr^2$) is typically:
(a) a protecting group that forms a thioether to protect a thiol group, for example a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamanthyl, $C_1$-$C_6$ acyloxymethyl (for example pivaloyloxymethyl, tertiary butoxycarbonyloxymethyl);
(b) a protecting group that forms a monothio, dithio or aminothioacetal to protect a thiol group, for example $C_1$-$C_6$ alkoxymethyl (for example methoxymethyl, isobutoxymethyl), tetrahydropyranyl, benzylthiomethyl, phenylthiomethyl, thiazolidine, acetamidemethyl, benzamidomethyl;
(c) a protecting group that forms a thioester to protect a thiol group, such as tertiary butoxycarbonyl (BOC), acetyl and its derivatives, benzoyl and its derivatives; or
(d) a protecting group that forms a carbamine acid thioester to protect a thiol group, such as carbamoyl, phenylcarbamoyl, $C_1$-$C_6$ alkylcarbamoyl (for example methylcarbamoyl and ethylcarbamoyl).

Typically, $Pr^1$ and $Pr^2$ are the same or different and each represent hydrogen or a protecting group that forms a thioether, a monothio, dithio or aminothioacetal, a thioester or a carbamine acid thioester to protect a thiol group. Preferably, $Pr^1$ and $Pr^2$ are the same or different and each represent hydrogen or a protecting group selected from a benzyl group which is optionally substituted by $C_1$-$C_6$ alkoxy (for example methoxy), $C_1$-$C_6$ acyloxy (for example acetoxy), hydroxy or nitro, picolyl, picolyl-N-oxide, anthrylmethyl, diphenylmethyl, phenyl, t-butyl, adamanthyl, $C_1$-$C_6$ acyloxymethyl (for example pivaloyloxymethyl, or t-butoxycarbonyloxymethyl), $C_1$-$C_6$ alkoxymethyl (for example methoxymethyl or isobutoxymethyl), tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl or $C_1$-$C_6$ alkylcarbamoyl (for example methylcarbamoyl and ethylcarbamoyl). Most preferably, $Pr^1$ and $Pr^2$ are hydrogen.

A hydroxyl-protecting group (for $Pr^3$) is typically:
(a) a protecting group that forms an ether to protect a hydroxyl group, for example a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamanthyl, $C_1$-$C_6$ acyloxymethyl (for example pivaloyloxymethyl, tertiary butoxycarbonyloxymethyl);
(b) a protecting group that forms an acetal or aminoacetal, for example $C_1$-$C_6$ alkoxymethyl (for example methoxymethyl, isobutoxymethyl), tetrahydropyranyl, acetamidemethyl, benzamidomethyl;
(c) a protecting group that forms an ester to protect a hydroxyl group, such as tertiary butoxycarbonyl (BOC), acetyl and its derivatives, benzoyl and its derivatives; or
(d) a protecting group that forms a carbamine acid ester to protect a hydroxyl group, such as carbamoyl, phenylcarbamoyl, $C_1$-$C_6$ alkylcarbamoyl (for example methylcarbamoyl and ethylcarbamoyl).

Typically, $Pr^3$ represents hydrogen or a protecting group that forms an ether, an acetal or aminoacetal, an ester or a carbamine acid ester to protect a hydroxyl group. Preferably, $Pr^3$ represents hydrogen or a protecting group selected from a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamanthyl, $C_1$-$C_6$ acyloxymethyl (for example pivaloyloxymethyl, tertiary butoxycarbonyloxymethyl), $C_1$-$C_6$ alkoxymethyl (for example methoxymethyl, isobutoxymethyl), tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl and $C_1$-$C_6$ alkylcarbamoyl (for example methylcarbamoyl and ethylcarbamoyl). Most preferably, $Pr^3$ is hydrogen.

In one embodiment, the amino acid side chain moieties are those derived from natural amino acids. Examples of amino acid side chain moieties derived from natural amino acids, with the amino acids from which they are derived shown in brackets, are —H (Glycine), —$CH_3$ (Alanine), —$CH(CH_3)_2$ (Valine), —$CH_2CH(CH_3)_2$ (Leucine), —$CH(CH_3)CH_2CH_3$ (Isoleucine), —$(CH_2)_4NH_2$ (Lysine), —$(CH_2)_3NHC(=NH)NH_2$ (Arginine), —$CH_2$-(5-1H-imidazolyl) (Histidine), —$CH_2CONH_2$ (Asparagine), —$CH_2CH_2CONH_2$ (Glutamine), —$CH_2COOH$ (Aspartic acid), —$CH_2CH_2COOH$ (Glutamic acid), —$CH_2$-phenyl (Phenylalanine), —$CH_2$-(4-OH-phenyl) (Tyrosine), —$CH_2$-(3-1H-indolyl) (Tryptophan), —$CH_2SH$ (Cysteine), —$CH_2CH_2SCH_3$ (Methionine), —$CH_2OH$ (Serine), and —$CH(OH)CH_3$ (Threonine).

In one embodiment, each amino acid side chain is an amino acid side chain moiety present in a natural amino acid or is —$(CH_2)_2$—$C(O)$—O—$C(CH_3)_3$ (tert-butoxycarbonylmethylanaline), —$(CH_2)_4$—NH—$C(O)$—O—$C(CH_3)_3$ ($N_\epsilon$-(tert-butoxycarbonyl)-lysine), —$(CH_2)_3$—NH—$C(O)NH_2$ (citrulline), —$CH_2$—$CH_2OH$ (homoserine) or —$(CH_2)_2$—$CH_2NH_2$ (ornithine).

In a preferred embodiment of the invention, each of $R_1$, $R_2$, $R_3$ and $R_4$ is the same or different and is a moiety selected from —H, —$C_1$-$C_6$ alkyl, —$C_2$-$C_6$ alkenyl, -L-O—C(O)—R', -L-C(O)—O—R", -L-A, -L-NR"R", -L-Het-C(O)-Het-R" and -L-Het-R", wherein L is a $C_1$-$C_6$ alkylene group, A is phenyl or a 5- to 6-membered heteroaryl group, each R' is the same or different and represents $C_1$-$C_4$ alkyl, each R" is the same or different and represents H or $C_1$-$C_6$ alkyl, each -Het- is the same or different and is a heteroatom spacer selected from —O—, —N(R''')- and —S—, and each R''' is the same or different and represents H or $C_1$-$C_4$ alkyl.

When the group A is a 5 to 6 membered heteroaryl group, it may, for example, be furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazyl, pyrimidinyl, pyrazinyl, triazinyl. Typically, however, each A moiety is phenyl.

The hetero atom spacer group Het is typically —O— or —N(R''')-. More typically it is —O— or —N(H)—. Preferably, each amino acid side chain is a moiety selected from —H, —$C_1$-$C_6$ alkyl, -L-C(O)—O—R", -L-A, -L-NR"R" and -L-N(R")—C(O)—O—R", wherein L, A and R" are as defined above.

Typically, $R_1$, $R_2$, $R_3$ and $R_4$ are independently selected from —$(CH_2)_2$—$C(O)$—O—$C(CH_3)_3$, —$(CH_2)_4$—NH—C(O)—O—$C(CH_3)_3$, —$(CH_2)_2$—C(O)OH, —$CH_2$—$C_6H_5$, —H, —$CH_3$, —$CH(CH_3)_2$, —$CH_2CH(CH_3)_2$, —$CH(CH_3)CH_2CH_3$, —$(CH_2)_4NH_2$, $CH_2SH$, —$CH_2CH_2SCH_3$, —$CH_2OH$ and —$CH(OH)CH_3$. More typically, the amino acid side chain moieties are selected from —H, —$CH_3$, —$CH(CH_3)_2$, —$CH_2CH(CH_3)_2$, —$CH(CH_3)CH_2CH_3$, —$(CH_2)_4NH_2$, $CH_2SH$, —$CH_2CH_2SCH_3$, —$CH_2OH$ and —$CH(OH)CH_3$.

Preferably, $R_1$, $R_2$, $R_3$ and $R_4$ are independently selected from —H, —$CH_3$, —$(CH_2)_2$—C(O)—O—C($CH_3$)$_3$, —$(CH_2)_4$—NH—C(O)—O—C($CH_3$)$_3$, —$(CH_2)_2$—C(O)OH, —$CH_2$—$C_6H_5$, —$(CH_2)_4NH_2$ and —CH($CH_3$)$_2$. In one embodiment of the invention, the amino acid side chain moieties are selected from —H, —$CH_3$ and —CH($CH_3$)$_2$.

Typically, $R_1$ is an amino acid side chain moiety selected from —H, —$C_1$-$C_6$ alkyl, —$C_2$-$C_6$ alkenyl, -L-O—C(O)—R', -L-C(O)—O—R", -L-A, -L-NR"R''', -L-Het-C(O)-Het-R" and -L-Het-R", wherein L, R', R", -Het- and R''' are as defined above. Preferably, $R_1$ is a moiety selected from —H, —$C_1$-$C_6$ alkyl, -L-C(O)—O—R", -L-A, -L-NR"R''' and -L-N(R")—C(O)—O—R", wherein L, A and R" are as defined above. More preferably, $R_1$ is a moiety selected from —H and —$C_1$-$C_6$ alkyl. More preferably still, $R_1$ is —$C_1$-$C_4$ alkyl or -L-A, in particular isopropyl or benzyl.

Typically, $R_2$ is a side chain moiety selected from —H, —$C_1$-$C_6$ alkyl, —$C_2$-$C_6$ alkenyl, -L-O—C(O)—R', -L-C(O)—O—R", -L-A, -L-NR"R''', -L-Het-C(O)-Het-R" and -L-Het-R", wherein L, R', R", -Het- and R''' are as defined above. Preferably, $R_2$ is a moiety selected from —H, —$C_1$-$C_6$ alkyl, -L-C(O)—O—R", -L-A, -L-NR"R''' and -L-N(R")—C(O)—O—R", wherein L, A and R" are as defined above. More preferably, $R_2$ is a moiety selected from —H and —$C_1$-$C_4$ alkyl. More preferably still, $R_2$ is —H, —$CH_3$ or —CH($CH_3$)$_2$. Even more preferably, $R_2$ is —H or —$CH_3$.

Typically, $R_3$ is an amino acid side chain moiety selected from —H, —$C_1$-$C_6$ alkyl, —$C_2$-$C_6$ alkenyl, -L-O—C(O)—R', -L-C(O)—O—R", -L-A, -L-NR"R''', -L-Het-C(O)-Het-R" and -L-Het-R", wherein L, R', R", -Het- and R''' are as defined above. Preferably, $R_3$ is a moiety selected from —H, —$C_1$-$C_6$ alkyl, -L-C(O)—O—R", -L-A, -L-NR"R''' and -L-N(R")—C(O)—O—R", wherein L, A and R" are as defined above.

More preferably, $R_3$ is —$CH_2$—$C_6H_5$, —$CH_2$-(3-1-t-butyloxycarbonyl-indolyl), —$CH_3$ or —$CH_2CH(CH_3)_2$.

Typically, $R_4$ is a side chain moiety selected from —H, —$C_1$-$C_6$ alkyl, —$C_2$-$C_6$ alkenyl, -L-O—C(O)—R', -L-C(O)—O—R", -L-A, -L-NR"R''', -L-Het-C(O)-Het-R" and -L-Het-R", wherein L, R', R", -Het- and R''' are as defined above. Preferably, $R_4$ is a moiety selected from —H, —$C_1$-$C_6$ alkyl, -L-C(O)—O—R", -L-A, -L-NR"R''' and -L-N(R")—C(O)—O—R", wherein L, A and R" are as defined above. More preferably, $R_4$ is hydrogen, —$C_1$-$C_6$ alkyl or —$C_2$-$C_6$ alkenyl. More preferably still, $R_4$ is hydrogen or —$C_1$-$C_4$ alkyl, more preferably hydrogen.

Typically, each $R_6$ is the same or different and is hydrogen or —$C_1$-$C_2$ alkyl. Preferably, each $R_6$ is hydrogen.

Preferred compounds of the invention are Spiruchostatin analogues as defined above wherein $R_1$ is selected from —H and —$C_1$-$C_6$ alkyl and -L-A, wherein L and A are as defined above, $R_2$ is selected from —H and —$C_1$-$C_4$ alkyl, $R_3$ is selected from —H, —$C_1$-$C_6$ alkyl, -L-A, wherein L and A are as defined above, $R_4$ is selected from —H and —$C_1$-$C_6$ alkyl and each $R_6$ is the same or different and is hydrogen or —$C_1$-$C_2$ alkyl, isosteres thereof and pharmaceutically acceptable salts thereof.

Further preferred compounds of the invention are (a) compounds of formula (I) wherein $R_1$ is —$C_1$-$C_4$ alkyl and L-A, $R_2$ is selected from —H and —$CH_3$, $R_3$ is selected from —H, —$C_1$-$C_6$ alkyl and -L-A, wherein L and A are as defined above, $R_4$ is —H and each $R_6$ is —H, isosteres thereof and pharmaceutically acceptable salts thereof, and (b) compounds of formula (I') wherein $R_1$ is —$C_1$-$C_4$ alkyl, $R_2$ is selected from —H and —$CH_3$, $R_3$ is selected from —H, —$C_1$-$C_6$ alkyl and -L-A, wherein L and A are as defined above, $R_4$ is —H, each $R_6$ is —H and $Pr^1$ and $Pr^2$ are hydrogen, isosteres thereof and pharmaceutically acceptable salts thereof.

Further preferred compounds are of the formulae:

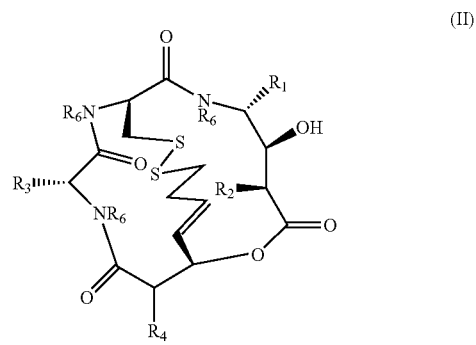

(II)

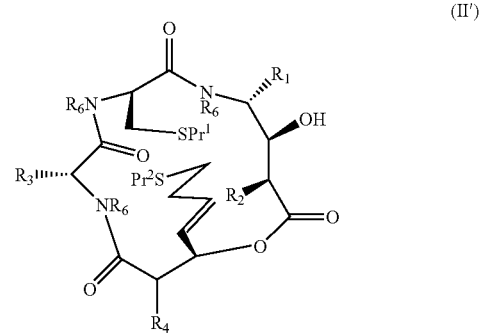

(II')

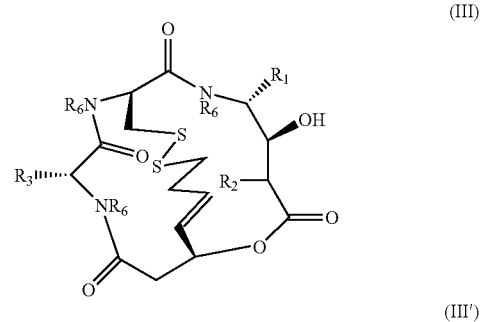

(III)

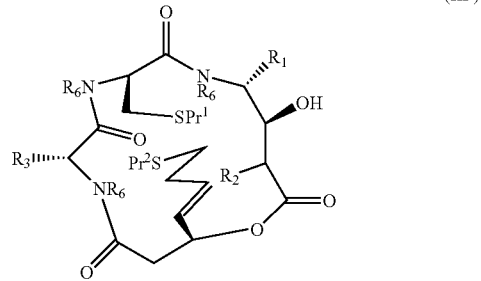

(III')

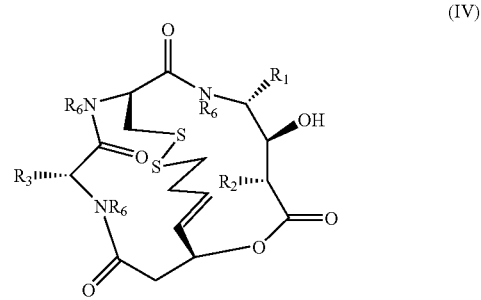

(IV)

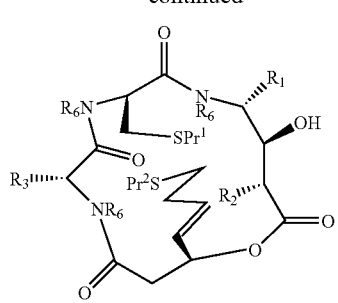

(IV')

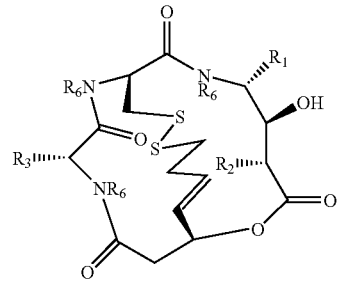

(V)

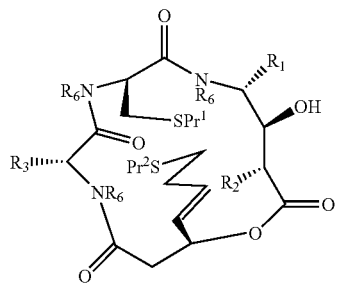

(V')

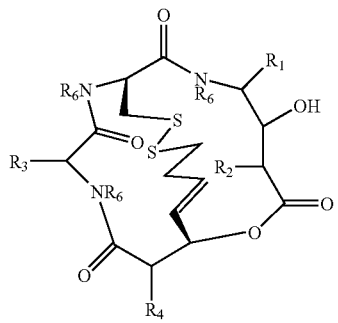

(VI)

Further particularly preferred compounds of formula (I) are those wherein $R_1$ is —CH(CH$_3$)$_2$, $R_2$ is —H, $R_3$ is —CH$_2$Ph, $R_4$ is hydrogen and $R_6$ is —H;

$R_1$ is —CH(CH$_3$)$_2$, $R_2$ is —H, $R_3$ is —CH$_2$-(3-1-t-butyloxycarbonyl-indolyl), $R_4$ is hydrogen and $R_6$ is —H;

$R_1$ is —CH(CH$_3$)$_2$, $R_2$ is —H, $R_3$ is —CH$_2$CH(CH$_3$)$_2$, $R_4$ is hydrogen and $R_6$ is —H;

$R_1$ is —CH$_2$Ph, $R_2$ is —H, $R_3$ is —CH$_2$C$_6$H$_5$, $R_4$ is hydrogen and $R_6$ is —H; or $R_1$ is —CH$_2$Ph, $R_2$ is —H, $R_3$ is —CH$_3$, $R_4$ is hydrogen and $R_6$ is —H; and pharmaceutically acceptable salts thereof.

Further particularly preferred compounds of formula (I') are those wherein $R_1$ is —CH(CH$_3$)$_2$, $R_2$ is —H, $R_3$ is —CH$_2$Ph, $R_4$ is hydrogen, $R_6$ is —H and Pr$^1$ and Pr are hydrogen;

$R_1$ is —CH(CH$_3$)$_2$, $R_2$ is —H, $R_3$ is —CH$_2$-(3-1-t-butyloxycarbonyl-indolyl), $R_4$ is hydrogen, $R_6$ is —H and Pr$^1$ and Pr$^2$ are hydrogen;

$R_1$ is —CH(CH$_3$)$_2$, $R_2$ is —H, $R_3$ is —CH$_2$CH(CH$_3$)$_2$, $R_4$ is hydrogen, $R_6$ is —H and Pr$^1$ and Pr$^2$ are hydrogen;

$R_1$ is —CH$_2$Ph, $R_2$ is —H, $R_3$ is —(CH$_2$)—C$_6$H$_5$, $R_4$ is hydrogen, $R_6$ is —H and Pr$^1$ and Pr$^2$ are hydrogen; or $R_1$ is —CH$_2$Ph, $R_2$ is —H, $R_3$ is —CH$_3$, $R_4$ is hydrogen, $R_6$ is —H and Pr$^1$ and Pr$^2$ are hydrogen; and pharmaceutically acceptable salts thereof.

Yet further preferred compounds are of formulae (2) to (14), (2') to (14'), (9"), (9'''), (12"), (14"), (14'''), (14'''') and (14''''').

Typically, in the embodiment of formula VI, $R_1$ and/or $R_2$ and/or $R_3$ is an amino acid side chain moiety derived from a natural amino acid. Preferably, $R_1$ is —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, —CH$_2$SH, —CH$_2$CH$_2$SCH$_3$, —CH$_2$OH or —CH(OH)CH$_3$. More preferably, $R_1$ is —H, —CH$_3$, —CH(CH$_3$)$_2$, —CH$_2$CH(CH$_3$)$_2$ or —CH(CH$_3$)CH$_2$CH$_3$. Most preferably, $R_1$ is —CH(CH$_3$)$_2$.

Preferably, $R_2$ is —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, —CH$_2$SH, —CH$_2$CH$_2$SCH$_3$, —CH$_2$OH or —CH(OH)CH$_3$. More preferably, $R_2$ is —H, —CH$_3$ or —CH(CH$_3$)$_2$. Most preferably, $R_2$ is —H.

Preferably, $R_3$ is —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, —CH$_2$SH, —CH$_2$CH$_2$SCH$_3$, —CH$_2$OH or —CH(OH)CH$_3$. More preferably, $R_3$ is —H, —CH$_3$, —CH(CH$_3$)$_2$, —CH$_2$CH(CH$_3$)$_2$ or —CH(CH$_3$)CH$_2$CH$_3$. Most preferably, $R_3$ is —CH$_2$Ph.

Typically, in this embodiment, $R_4$ is hydrogen or $C_1$-$C_6$ alkyl. Preferably, $R_4$ is hydrogen or $C_1$-$C_2$ alkyl. More preferably, $R_4$ is hydrogen.

In this embodiment, preferred compounds of the invention are compounds of formula (VI) wherein:

$R_1$ is —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, —CH$_2$SH, —CH$_2$CH$_2$SCH$_3$, —CH$_2$OH or —CH(OH)CH$_3$;

$R_2$ is —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, —CH$_2$SH, —CH$_2$CH$_2$SCH$_3$, —CH$_2$OH or —CH(OH)CH$_3$;

$R_3$ is —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, —CH$_2$SH, —CH$_2$CH$_2$SCH$_3$, —CH$_2$OH or —CH(OH)CH$_3$; and $R_4$ is —H, —CH$_3$, —CH(CH$_3$)$_2$, —CH$_2$CH(CH$_3$)$_2$, —CH(CH$_3$)CH$_2$CH$_3$, —(CH$_2$)$_4$NH$_2$, —CH$_2$SH, —CH$_2$CH$_2$SCH$_3$, —CH$_2$OH or —CH(OH)CH$_3$.

In a preferred aspect of this embodiment, compounds of formula (VI) are those wherein:

$R_1$ is —H, —CH$_3$, —CH(CH$_3$)$_2$, —CH$_2$CH(CH$_3$)$_2$ or —CH(CH$_3$)CH$_2$CH$_3$;

$R_2$ is —H, —CH$_3$ or —CH(CH$_3$)$_2$;

$R_3$ is —H, —CH$_3$, —CH(CH$_3$)$_2$, —CH$_2$CH(CH$_3$)$_2$ or —CH(CH$_3$)CH$_2$CH$_3$; and $R_4$ is hydrogen.

Particularly preferred compounds of this embodiment are those of formula (VI) wherein $R_1$ is —CH(CH$_3$)$_2$, $R_2$ is —H, $R_3$ is —CH$_2$C$_6$H$_5$ and $R_4$ is —H.

The compounds of the present invention are particularly advantageous since they show desirable therapeutic effects. They are also advantageous since the peptide core can be readily synthesised.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines or heterocyclic amines.

As used herein, the term "isostere" refers to a compound resulting from the exchange of an atom or a group of atoms with another, broadly similar, atom or group of atoms. In the compounds of the invention, the moieties which contain isosteric groups are preferably —NH—CHR$_1$—CO—, —NH—CHR$_2$—CO—O— and —NH—CO—CHR$_3$—NH—CO—. In the compounds of the invention, the moieties which contain isosteric groups are more preferably —NH—CHR$_1$—CO— and —NH—CHR$_2$—CO—O—. Examples of such isosteres are compounds of formula (I) wherein the moiety —NH— has been replaced by —CH$_2$—, —O— or —S—, the moiety —CO— has been replaced by —CS— or —C(=NH)— and the moiety —O— has been replaced by —S—, CH$_2$— or —NH—.

The compounds of the present invention have the chirality shown in formula (I). However, the spatial positioning of the groups R$_1$, R$_2$ and R$_3$ can result in the formation of additional chiral centres in the compounds. For the avoidance of doubt, the chemical structures depicted herein are intended to embrace all of the stereoisomeric configurations associated with these additional chiral centres, including racemic and non-racemic mixtures and pure enantiomers and/or diastereoisomers.

For the avoidance of doubt, the present invention also embraces prodrugs which react in vivo to give a compound of the present invention or an isostere or pharmaceutically acceptable salt thereof.

Preferred compounds of the invention are optical isomers. Thus, for example, preferred compounds of formula (I) containing only one chiral centre include an R isomer in substantially pure form, an S enantiomer in substantially pure form and enantiomeric mixtures which contain an excess of the R enantiomer or an excess of the S enantiomer.

The present invention also provides a compound of formula (I), an isostere thereof or a pharmaceutically acceptable salt thereof and a pharmaceutically acceptable carrier or diluant.

Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer. Preferably, the pharmaceutical composition comprises a pharmaceutically acceptable salt of a compound of formula (I) or an isostere thereof.

The Spiruchostatin analogues may be prepared by conventional routes, for example using the following scheme wherein the groups R$_1$ to R$_4$ are as defined above:

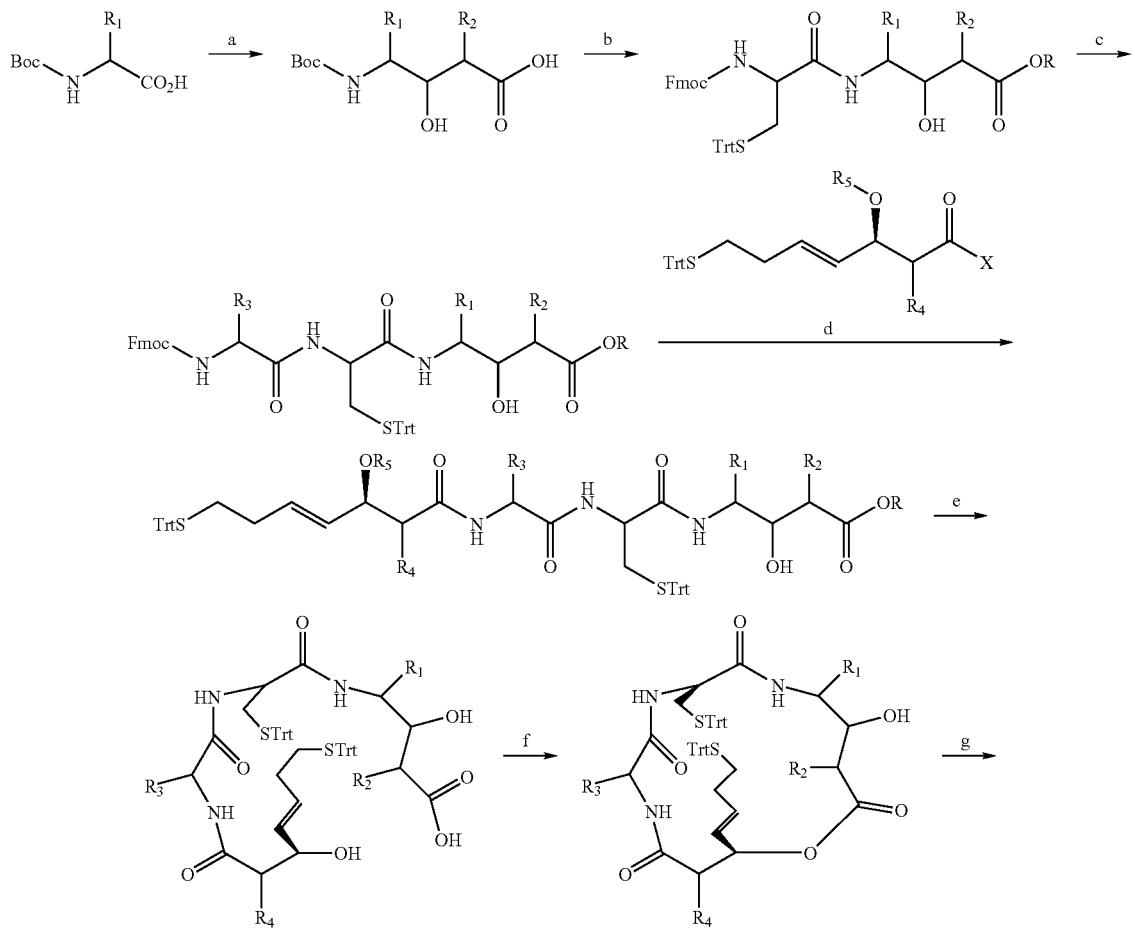

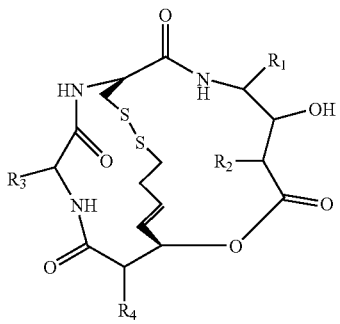

In step (a), an amino acid bearing the side-chain $R_1$ is condensed with an ester enolate bearing the side-chain $R_2$ and then reduced to give a statine unit. In step (b), the statine is condensed with a protected cysteine derivative to give a tripeptide isostere. In step (c) the tripeptide isostere is coupled with an amino acid to provide a protected tetrapeptide isostere. In step (d), the N-terminus of the peptide is deprotected, and the free amine is coupled with a β-hydroxy acid derivative wherein $R_5$ is a temporary blocking group which can be removed to produce a compound wherein $R_5$ is H, and X is a chiral auxiliary as reported in Yurek-George, A.; Habens, F.; Brimmell, M.; Packham, G.; Ganesan, A. *J. Am. Chem. Soc.* 2004, 126, 1030-1031. In step (e), the ester group is hydrolysed, followed by cyclization in step (f) and disulfide bond formation in (g) to complete the synthesis of the bicyclic depsipeptide compounds (I).

Compounds of the invention in which $R_6$ is other than hydrogen can be obtained either by alkylating a corresponding compound of the invention or intermediate in which $R_6$ is hydrogen or by using appropriately substituted starting materials.

Compounds of formula (I') may be obtained by reaction of the product of step (g) above to cleave the disulfide bond. The cleavage of the disulfide bond is typically achieved using a thiol compound generally used for a reduction treatment of a protein having a disulfide bond, for example mercaptoethanol, thioglycol acid, 2-mercaptoethylamine, benzenethiol, parathiocresol and dithiothreitol. Preferably, mercaptoethanol and dithiothreitol are used. An excess thiol compound can be removed by for example dialysis or gel filtration. Alternatively, electrolysis, sodium tetrahydroborate, lithium aluminum hydride or sulfite may, for example, be used to cleave the disulfide bond.

Compounds of formula (I') in which $Pr^1$ and/or $Pr^2$ is other than hydrogen may be prepared by introducing a thiol-protecting group into a corresponding compound in which $Pr^1$ and/or $Pr^2$ is/are hydrogen. In this aspect a suitable agent for introducing thiol-protecting group to be used in this reaction is appropriately determined depending on the protecting group to be introduced. Examples include chlorides of the corresponding protecting group (for example benzyl chloride, methoxybenzyl chloride, acetoxybenzyl chloride, nitrobenzyl chloride, picolyl chloride, picolyl chloride-N-oxide, anthryl methyl chloride, isobutoxymethyl chloride, phenylthiomethyl chloride) and alcohols of the corresponding protecting group (for example diphenylmethyl alcohol, adamanthyl alcohol, acetamidemethyl alcohol, benzamidomethyl alcohol), dinitrophenyl, isobutylene, dimethoxymethane, dihydropyran and t-butyl chloroformate.

As the skilled person will appreciate, when one of $R_1$, $R_2$, $R_3$ and $R_4$ carries a functional group such as —OH, —SH, —NH$_2$ or —COOH, then it may be preferred for that group to be protected for one more of the reaction steps following its introduction. In this case the group in question could be protected in a separate step after its introduction, or, it could be protected already at the time it is introduced. The skilled person will be aware of suitable protecting groups that can be used in this regard.

The thus obtained Spiruchostatin analogues may be salified by treatment with an appropriate acid or base. Racemic mixtures obtained by any of the above processes can be resolved by standard techniques, for example elution on a chiral chromatography column.

Preferred compounds of the invention have an HDAC inhibitory activity which is at least equal to that exhibited by Suberoylanilide hydroxamic acid (SAHA). Thus, in a further embodiment, the present invention provides a process for selecting a compound which has an HDAC inhibitory activity which is at least equal to that exhibited by SAHA, which process comprises preparing a compound of formula (I) or (I') by:

(i) reacting a compound of formula (VI) with a compound of formula (VII)

(VI)

(VIII)

wherein $R_1$ and $R_2$ are as defined above, $R_7$ is $C_1$-$C_4$ alkyl or $C_2$-$C_4$ alkenyl and Y is an amino protecting group;

(ii) deprotecting the thus obtained intermediate and reacting it with a compound of formula (VIII)

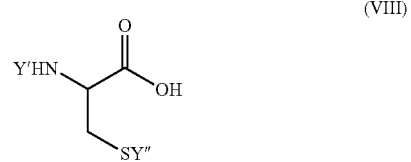

(VIII)

wherein Y' is an amino protecting group and Y" is hydrogen or a protecting group;

(iii) deprotecting the thus obtained intermediate and reacting it with a compound of formula (IX)

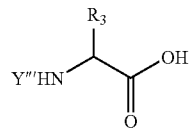

(IX)

wherein $R_3$ is as defined above and Y''' is an amino protecting group;

(iv) deprotecting the thus obtained intermediate and reacting it with a compound of formula (X)

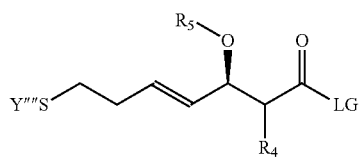

(X)

wherein $R_4$ is as defined above, $R_5$ is hydrogen or a hydroxy protecting group, LG is a leaving group and Y'''' is hydrogen or a protecting group;

(v) optionally deprotecting the β-hydroxy group on the thus obtained intermediate to remove the $R_5$ protecting group and replace it with H;

(vi) hydrolysing and cyclizing the thus obtained intermediate;

(vii) optionally reacting the thus obtained intermediate to effect disulfide bond formation, and, if a disulfide bond is formed, optionally cleaving the disulfide bond in the thus obtained compound, and if the thus obtained compound contains a thiol group, optionally introducing a thiol-protecting group; and (viii) screening the thus obtained compound to measure its activity as an HDAC inhibitor.

Typically, in step (vi), hydrolysis of the ester group is effected before cyclisation.

Typically, in step (vii), DTT (dithiothreitol) is used to effect cleavage of the disulfide bond.

The person of skill in the art will appreciate that various identities may be used for the protecting groups Y, Y', Y'', Y''' and Y'''', and that the preferred identity will depend in each case on the nature of the particular groups present.

The groups Y, Y' and Y''' may, for example, be t-butoxycarbonyl (Boc) or 9-fluorenylmethoxycarbonyl (Fmoc). Typically, they are Fmoc.

The groups Y'' and Y'''' may, for example, be trityl (Trt).

The skilled person will be aware of suitable identities for the leaving group LG. It may, for example, be a chiral auxiliary, such as a thiazolidinethione group attached via its N atom, as explained in Yurek-George, A. et al (*J. Am. Chem. Soc.* 2004, 126, 1030-1031). Alternatively, it may be a —OH group.

The group $R_7$ is typically a $C_1$-$C_4$ alkyl or $C_1$-$C_4$ alkenyl group. More typically, it is methyl or allyl.

The skilled person will appreciate that various assays are suitable for testing for HDAC inhibition and may be used to measure the activity of a compound obtained from step (vii) compared to that of the known HDAC inhibitor SAHA. Thus, the $IC_{50}$ of a test compound against HDAC can, for example, be determined in an in vitro assay, and compared with the $IC_{50}$ of SAHA under the same assay conditions. If a test compound has an $IC_{50}$ value equal to or lower than that of SAHA it should be understood as having an HDAC inhibitory activity which is at least equal to that exhibited by SAHA.

In a preferred embodiment, the present invention provides a process for selecting a compound which has an HDAC inhibitory activity which is at least equal to that exhibited by SAHA as defined above, wherein in step (viii) the screening step is an in vitro HDAC assay. Typically, said assay comprises contacting a test compound and SAHA, at various concentrations, with diluted Hela Nuclear Extract to determine the $IC_{50}$ of the test compound and of SAHA against Hela Nuclear Extract. A test compound which has an $IC_{50}$ value measured against Hela Nuclear Extract which is equal to, or lower than, the $IC_{50}$ of SAHA under the same assay conditions should be understood as having an inhibitory activity which is at least equal to that exhibited by SAHA. Typically, the assay is performed using a HDAC fluorescent activity assay kit (Biomol, UK) and the test compounds are reduced prior to analysis. Said assay test may, for example, be performed as described below under the heading "Activity Assay 1".

In another embodiment, the present invention provides a process for selecting a compound which has a human cancer cell growth inhibitory activity which is at least equal to that exhibited by SAHA, which process comprises preparing a compound of formula (I) or (I') via steps (i) to (vii) as defined above followed by (viii) screening the compound to measure its activity as a human cancer cell growth inhibitor.

The skilled person will appreciate that various assays are suitable for testing for human cancer cell growth inhibition and may be used to measure the activity of a compound obtained from step (vii) compared to that of SAHA. Thus, the $IC_{50}$ of a test compound against human cancer cell growth can, for example, be determined in an in vitro assay, and compared with the $IC_{50}$ of SAHA under the same assay conditions. If a test compound has an $IC_{50}$ value equal to or lower than that of SAHA it should be understood as having an inhibitory activity which is at least equal to that exhibited by SAHA. Typically in this embodiment step (viii) comprises an in vitro assay which comprises contacting a test compound and SAHA, at various concentrations, with an MCF7 breast, HUT78 T-cell leukaemia, A2780 ovarian, PC3 or LNCAP prostate cancer cell line to determine the $IC_{50}$ of the test compound and of SAHA against the cell line. A test compound which has an $IC_{50}$ value measured against any of these cell lines which is equal to, or lower than, the $IC_{50}$ of SAHA under the same assay conditions should be understood as having an inhibitory activity at least equal to that of SAHA. Typically in this embodiment, said assay is performed using the CyQuant™ assay system (Moelcular Probes, Inc. USA). Said assay test may, for example, be performed as described below under the headings "Activity Assay 2".

In another preferred embodiment, the present invention provides a process for selecting a compound which has an anti-inflammatory activity which is at least equal to that exhibited by SAHA, which process comprises preparing a compound of formula (I) or (I') via steps (i) to (vii) as defined above followed by (viii) screening the compound to measure its anti-inflammatory activity.

The skilled person will appreciate that various assays are suitable for assessing the anti-inflammatory activity of a compound. The anti-inflammatory activity of a test compound relative to SAHA may, for example, be determined by measuring the activity of a compound in inhibiting the production of TNFα from peripheral blood mononuclear cells (PBMCs) relative to SAHA. Thus, the ability of a test compound to inhibit the production of TNFα from PBMCs can, for example, be determined in an assay, and compared with the activity of SAHA under the same assay conditions. If a test compound has an in vitro inhibitory activity of TNFα production which is equal to or higher than that of SAHA under the same assay conditions it should be understood as having an anti-inflammatory activity which is at least equal to that exhibited by SAHA. Typically step (viii) is performed using the Quantikine® Human-α assay kit (R&D systems, Abingdon UK). Said assay test may, for example, be performed as described below under the heading "Activity Assay 3".

In another aspect of this embodiment, the anti-inflammatory activity of a test compound relative to SAHA may be determined by assessing the activity of a compound in inhibiting inflammation in Balb/c mice relative to SAHA. If a test compound has an in vivo inhibitory activity which is equal to or higher than that of SAHA under the same test conditions, it should be understood as having an anti-inflammatory activity which is at least equal to that exhibited by SAHA. Typically, in this embodiment, step (viii) is performed by assessing the in vivo activity of a test compound and of SAHA in inhibiting inflammation in Balb/c mice induced by a chemical challenge. Typically, said chemical challenge involves the topical administration to the mice of oxalazone or acetone. In this embodiment, the compounds under investigation may be applied before or after the chemical challenge.

In another preferred embodiment, the present invention provides a process for selecting a compound which has an activity in inducing a predominant G2/M phase arrest or cell death in MCF7 cells which is at least equal to that exhibited by SAHA, which process comprises preparing a compound of formula (I) or (I') via steps (i) to (vii) as defined above followed by (viii) screening the thus obtained compound to measure activity in inducing a predominant G2/M phase arrest or cell death in MCF7 cells relative to SAHA.

In the screening steps described above, the preferred form of the test compound depends on the nature of the screening step. Thus, if the screening step is an in vitro assay such as that described below under "Assay Activity 1", the test compound is preferably of formula (I') as defined above. If, however, the screening step is against a cell line, then the test compound is preferably of the formula (I).

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal, transdermal or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

One preferred route of administration is inhalation. The major advantages of inhaled medications are their direct delivery to the area of rich blood supply in comparison to many medications taken by oral route. Thus, the absorption is very rapid as the alveoli have an enormous surface area and rich blood supply and first-pass metabolism is bypassed.

Preferred pharmaceutical compositions of the invention therefore include those suitable for inhalation. The present invention also provides an inhalation device containing such a pharmaceutical composition. Typically, said device is a metered dose inhaler (MDI), which contains a pharmaceutically acceptable chemical propellant to push the medication out of the inhaler. Typically, said propellant is a fluorocarbon.

Further preferred inhalation devices include nebulizers. Nebulizers are devices capable of delivering fine liquid mists of medication through a "mask" that fits over the nose and mouth, using air or oxygen under pressure. They are frequently used to treat those with asthma who cannot use an inhaler, including infants, young children and acutely ill patients of all ages.

Said inhalation device can also be, for example, a rotary inhaler or a dry powder inhaler, capable of delivering a compound of the invention without a propellant.

Typically, said inhalation device contains a spacer. A spacer is a device which enables individuals to inhale a greater amount of medication directly into the lower airways, where it is intended to go, rather than into the throat. Many spacers fit on the end of an inhaler; for some, the canister of medication fits into the device. Spacers with holding chambers and one-way valves prevent medication from escaping into the air. Many people, especially young children and the elderly, may have difficulties coordinating their inhalation with the action necessary to trigger a puff from a metered dose inhaler. For these patients, use of a spacer is particularly recommended.

Another preferred route of administration is intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. Drugs can be delivered nasally in smaller doses than medication delivered in tablet form. By this method absorption is very rapid and first pass metabolism is bypassed, thus reducing inter-patient variability. Nasal delivery devices further allow medication to be administered in precise, metered doses. Thus, the pharmaceutical compositions of the invention are typically suitable for intranasal administration. Further, the present invention also provides an intranasal device containing such a pharmaceutical composition.

A further preferred route of administration is transdermal administration. The present invention therefore also provides a transdermal patch containing a compound of the invention, or a pharmaceutically acceptable salt thereof. Also preferred is sublingual administration. The present invention therefore also provides a sub-lingual tablet comprising a compound of the invention or a pharmaceutically acceptable salt thereof.

A compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example, a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention are therapeutically useful in the treatment or prevention of conditions mediated by HDAC. Accordingly, the present invention provides the use of a compound of the formula (I), or a pharmaceutically acceptable salt thereof, in the manufacture of a medicament for use in the treatment or prevention of a condition mediated by HDAC. Also provided is a method of treating a patient suffering from or susceptible to a condition mediated by HDAC, which method comprises administering to said patient an effective amount of a compound of formula (I), an isostere thereof or a pharmaceutically acceptable salt thereof.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The present invention therefore provides a product comprising (a) a Spiruchostatin analogue of the invention as defined above or an isostere or pharmaceutically acceptable salt thereof; and (b) another known inhibitor of HDAC, such as SAHA, for simultaneous, separate or sequential use.

The present invention therefore also provides the use of a Spiruchostatin analogue of the invention as defined above or an isostere or pharmaceutically acceptable salt thereof for use in the manufacture of a medicament for use in co-administration with another known inhibitor of HDAC, such as SAHA.

The skilled person will be aware of other known inhibitors of HDAC. US20040266769, for example, gives suitable examples. Examples include Spiruchostatin A, FR-901228, trichostatin A and SAHA.

The compounds of the present invention can be used in both the treatment and prevention of cancer and can be used in a monotherapy or in a combination therapy. When used in a combination therapy, the compounds of the present invention are typically used together with small chemical compounds, radiation, antibody-based therapies (for example herceptin and rituximab), anti-cancer vaccination, gene therapy, cellular therapies, hormone therapies or cytokine therapy.

In a preferred embodiment of the invention, a compound of the invention is used in combination with another chemotherapeutic or antineoplastic agent in the treatment of a cancer. Examples of such other chemotherapeutic or antineoplastic agents include mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN 38, and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of a Spiruchostatin analogue as defined above or an isostere thereof or a pharmaceutically acceptable salt thereof in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition may be used to therapeutically address these disease states. Examples of various diseases that may be treated using the HDAC inhibitors of the present invention are described herein. It is noted that additional diseases beyond those disclosed herein may be later identified as the biological roles that HDAC play in various pathways becomes more fully understood.

One set of indications that HDAC inhibitors of the present invention may be used to treat are those involving undesirable or uncontrolled cell proliferation. Such indications include benign tumors, various types of cancers such as primary tumors and tumor metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta.-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumors retain their differentiated features and do not divide in a completely uncontrolled manner. A benign tumor is usually localized and non-metastatic. Specific types of benign tumors that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumors, or metastases, are tumors that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumors, either primary or secondary, that can be treated using the HDAC inhibitors of the present invention include, but are not limited to, leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome. An example of a cell proliferative disorder that may be treated using the invention is a bone tumor.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of retinal/choroidal neovascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi's sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra-intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angionesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arhthymia, hypercholestremia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumors, more preferably for the treatment of malignant tumors and most preferably for the treatment of CCL, breast cancer and T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes, osteoporosis, MDS, benign prostatic hyperplasia, oral leukoplakia, a genetically related metabolic disorder, an infection, Rubens-Taybi, fragile X syndrome, or alpha-1 antitrypsin deficiency, or to accelerate wound healing, to protect hair follicles or as an immunosuppressant.

The inflammatory condition may be, for example, a skin inflammatory condition (for example psoriasis, acne or eczema), asthma, chronic obstructive pulmonary disease (COPD), rheumatoid arthritis (RA), inflammatory bowel disease (IBD), Crohn's disease or colitis.

The cancer may be, for example, chronic lymphocytic leukaemia, breast cancer, prostate cancer, ovarian cancer, mesothelioma or T-cell lymphoma.

The cardiovascular disease may be, for example, hypertension, myocardial infarction (MI), ischemic heart disease (IHD) (reperfusion), angina pectoris, arrhythmia, hypercholestremia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

The genetically related metabolic disorder may be, for example, cystic fibrosis (CF), peroxisome biogenesis disorder or adrenoleukodystrophy.

Compounds of the invention may be used as an immunosuppressant following organ transplant.

The infection may be, for example, a viral, bacterial, fungal or parasitic infection, in particular an infection by *S. aureus, P. acne, Candida* or *Aspergillus.*

The CNS disorder may be, for example, Huntingdon's disease, Alzheimer's disease, multiple sclerosis or amyotrophic lateral sclerosis.

Preferably, compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

Most preferably, the compounds of the invention are used to alleviate chronic lymphocytic leukaemia, breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

A therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration. Preferably, daily dosage levels are from 5 mg to 2 g.

The following Examples illustrate the invention. The assays are designed only to provide an indication of activity in inhibiting HDAC. There are many assays available to determine the activity of given compounds as HDAC antagonists, and a negative result in any one particular assay is therefore not determinative.

In the following description, the structures of compounds were confirmed by various techniques, including NMR as appropriate (details not given).

Compounds of the invention were prepared by the following general scheme.

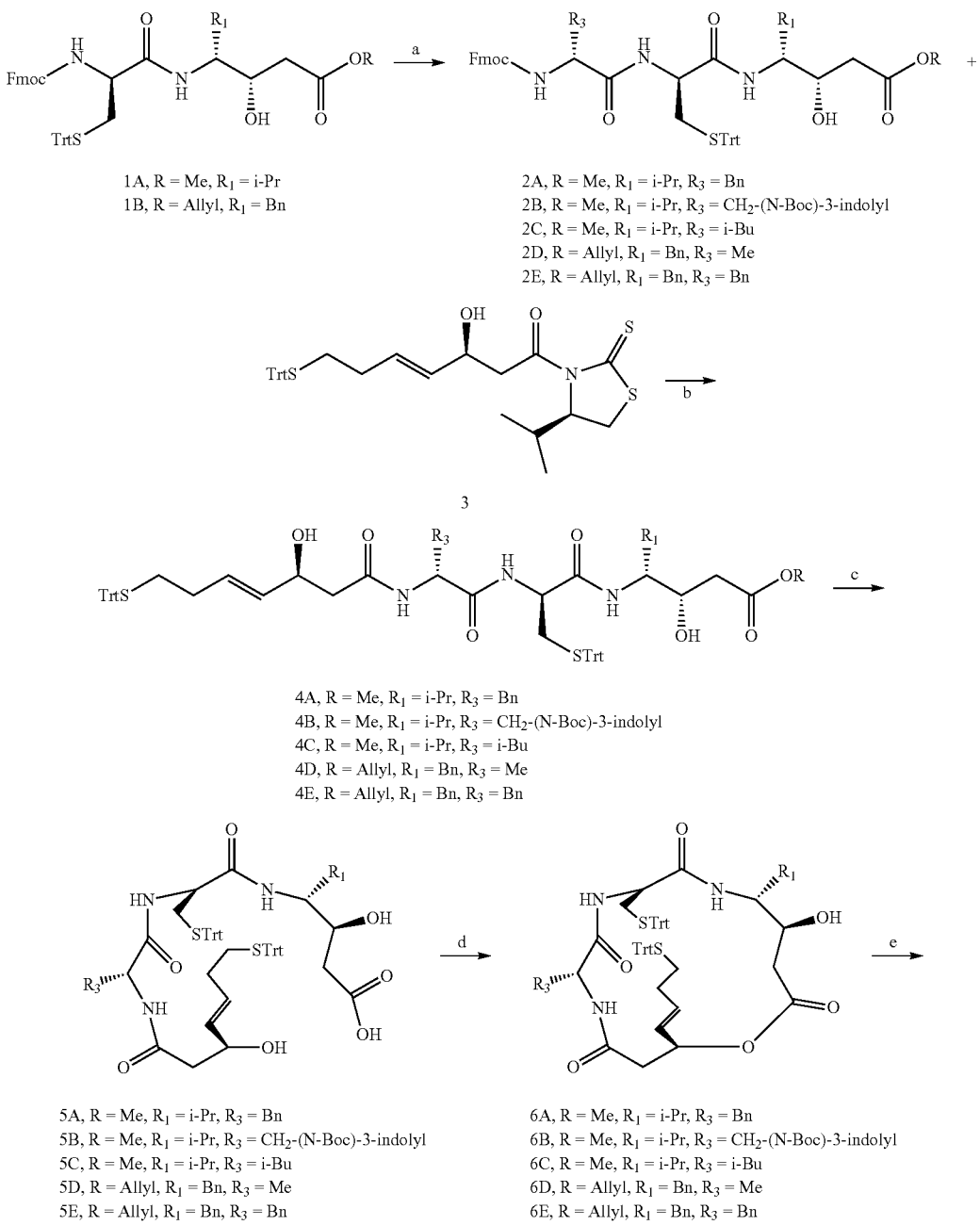

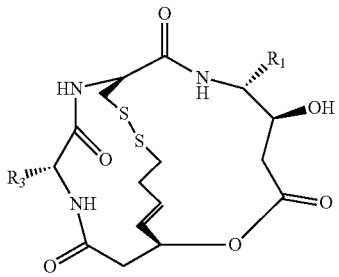

7A, R = Me, R₁ = i-Pr, R₃ = Bn
7B, R = Me, R₁ = i-Pr, R₃ = CH₂-(N-Boc)-3-indolyl
7C, R = Me, R₁ = i-Pr, R₃ = i-Bu
7D, R = Allyl, R₁ = Bn, R₃ = Me
7E, R = Allyl, R₁ = Bn, R₃ = Bn Preparation of (3S,4R)-4-{2-[(R)-2-(9H-fluoren-9-ylmethoxycarbonylamino)-3-phenyl-propionylamino]-3-tritylsulfanyl-propionylamino}-3-hydroxy-5-methyl-hexanoic acid allyl ester (2A)

(1:1); [α]²⁶_D=+2.65 (c 0.15, CHCl₃); IR (thin film) 3305 (br), 1708 (m), 1649 (s), 1539 (m), 1533 (m).

Preparation of (3S,4R)-3-Hydroxy-4-{2-[(R)-2-((Z)-(S)-3-hydroxy-7-tritylsulfanyl-hept-4-enoylamino)-3-phenyl-propionylamino]-3-tritylsulfanyl-propionylamino}-5-methyl-hexanoic acid allyl ester (4A)

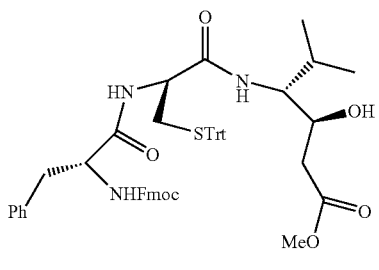

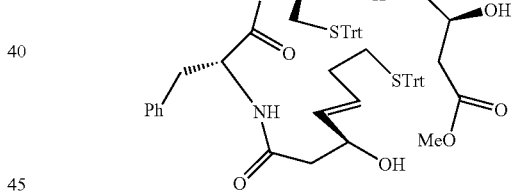

To a solution of 1A (190.4 mg, 0.25 mmol, prepared according to the procedure in Doi, T,; Iijima, Y.; Shin-ya, K.; Ganesan, A,; Takahashi, T.; *Tet. Lett.* 2006, 47, 1177-1080) in CH₃CN (9.5 mL) under argon was added diethylamine (0.5 mL, 5% v/v) and the reaction mixture stirred at room temperature for 1 h. The solvent was removed in vacuo, and this was repeated again adding hexane (3×10 mL). The crude amine was then dried under high vacuum for 40 min. Then to a solution of PyBop (185 mg, 0.36 mmol) and Fmoc-D-Phe-OH (139 mg, 0.36 mmol) in CH₂Cl₂ (4.75 mL) was added diisopropylethylamine (0.15 mL, 0.86 mmol) under argon with stirring. A solution of the resultant deprotected amine in CH₃CN (4.75 mL) was added and the reaction was allowed to stir at room temperature for 16 h. The solvent was then removed in vacuo. Purification by column chromatography on silica gel (eluent 1:1 EtOAc/Hexane) gave 2A (126 mg, 0.14 mmol, 55%) as a white solid: R_f 0.17 EtOAc/Hexane To a solution of 2A (582 mg, 0.64 mmol) in CH₃CN (25 mL) was added diethylamine (1 mL, 9.6 mmol) under argon. After 2 h the solvent was removed in vacuo and this was repeated with hexane (3×15 ml) after which time the crude material was put under a high vacuum (30 min). Then to a solution of the crude amine in CH₂Cl₂ (10 mL) was added DMAP (11 mg, 0.09 mmol) followed by a solution of alcohol 3 (492 mg, 0.88 mmol, prepared according to the procedure in Yurek-George, A.; Habens, F.; Brimmell, M.; Packham, G.; Ganesan, A. *J. Am. Chem. Soc.* 2004, 126, 1030-1031) in CH₂Cl₂ (15 mL). The reaction was then stirred for 16 h. The solvent was removed in vacuo and the solid formed was purified by column chromatography on silica gel (eluent 4:6-6:4 EtOAc/Hexane) to give 4A (389 mg, 0.35 mmol, 55%) as a white solid: $R_f$ 0.25 EtOAc/Hexane (1:1); $[\alpha]^{26}{}_D$=+ 0.85 (c 0.35, CHCl$_3$); IR (thin film) 3279 (br), 1733 (m), 1690 (m), 1656 (m), 1628 (s).

Preparation of (3S,4R)-3-hydroxy-4-((S)-2-{(S)-2-[((E)-(R)-1-hydroxy-5-tritylsulfanyl-pent-2-enylcarbamoyl)-methyl]-3-phenyl-propionylamino}-3-tritylsulfanyl-propionylamino)-5-methyl-hexanoic acid (5A)

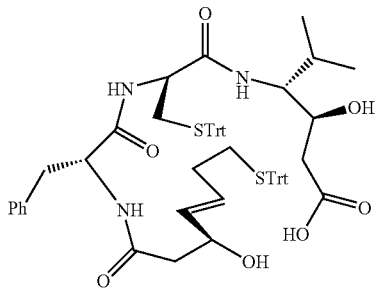

To a solution of 4A (383 mg, 0.35 mmol), Pd(PPh$_3$)$_4$ (41.2 mg, 0.036 mmol) in dry methanol (11 mL) under argon was added morpholine (62 µL, 0.71 mmol) which was allowed to stir for 3 h. The reaction mixture was concentrated in vacuo, CH$_2$Cl$_2$ (20 mL) was then added before washing with 1M HCl (15 mL), sat. sodium hydrogen carbonate (15 mL), sat. brine (15 mL), dried over MgSO$_4$ and concentrated in vacuo. Purification was then carried out by column chromatography on silica gel (eluent 5:95-6:94 MeOH/CH$_2$Cl$_2$) to give a white solid 5A (137 mg, 0.13 mmol, 37%). $R_f$ 0.12 MeOH/CH$_2$Cl$_2$ (5:95).

Preparation of (3R,7S,10S,13R,14S)-7-benzyl-14-hydroxy-13-isopropyl-3-((E)-4-tritylsulfanyl-but-1-enyl)-10-tritylsulfanylmethyl-1,2-dioxa-4,9,12-triaza-cyclohexadecane-5,8,11,16-tetraone (6A)

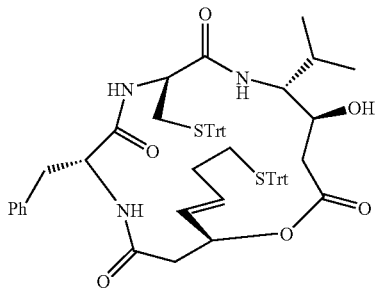

To a solution of MNBA (54 mg, 0.16 mmol) and DMAP (38 mg, 0.31 mmol) in CH$_2$Cl$_2$ (29 mL) was added dropwise a solution of the acid 5A (137 mg, 0.13 mmol) in CH$_2$Cl$_2$ (117 mL) over 4.5 h, this was then stirred overnight at room temperature. The reaction mixture was washed sequentially with HCl (1M, 40 mL), sodium hydrogen carbonate (40 ml) and sat. brine (40 mL) before being dried (MgSO$_4$), filtered and concentrated in vacuo to give a brown solid. Purification by column chromatography on silica gel (eluent 4:6-1:1 EtOAc/Hexane increased to 1:9 MeOH/CHCl$_3$) gave 6A (79.4 mg, 0.08 mmol, 58%) as a white/brown solid: $R_f$ 0.14 EtOAc/Hexane (4:6).

Preparation of (E)-(1R,6S,7R,10S,21S)-21-benzyl-6-hydroxy-7-isopropyl-2,3-dioxa-12,13-dithia-8,18,23-triaza-bicyclo[8.7.6]tricos-16-ene-4,9,19,22-tetraone (7A)

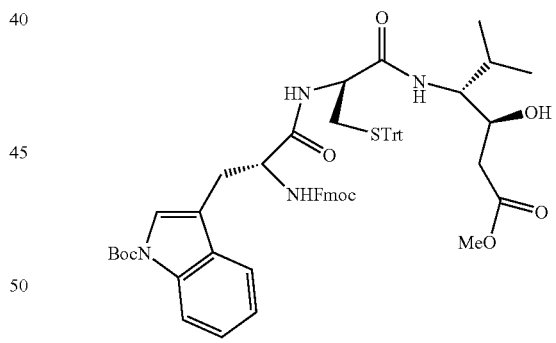

To a solution of iodine (198.4 mg, 0.78 mmol) in CH$_2$Cl$_2$/MeOH (9:1, 272 mL) was added dropwise a solution of 6A (79.4 mg, 0.08 mmol) in CH$_2$Cl$_2$/MeOH (9:1) (134 mL) over 30 min, the reaction mixture was then allowed to stir for a further 30 min after which time sodium thiosulfate (88 mL, 0.05 M) was added. The layers were separated and the product was extracted with CH$_2$Cl$_2$ (3×45 ml) dried (MgSO$_4$) and the solvent was removed in vacuo. Purification was then carried out by column chromatography on silica gel (eluent 3:97 MeOH/CH$_2$Cl$_2$) which gave 7A (30 mg, mmol, 68%) as a white solid: $R_f$ 0.19 CH$_2$Cl$_2$/MeOH (97:3); $[\alpha]^{26}{}_D$=−83.7 (c 0.38, MeOH).

Preparation of 3-[(R)-2-[(S)-1-((1R,2S)-3-Allyloxy-carbonyl-2-hydroxy-1-isopropyl-propylcarbamoyl)-2-tritylsulfanyl-ethylcarbamoyl]-2-(9H-fluoren-9-ylmethoxycarbonylamino)-ethyl]-indole-1-carboxylic acid tert-butyl ester (2B)

To a solution of 1A (398.1 mg, 0.52 mmol) in CH$_3$CN (20 mL) under argon was added diethylamine (0.96 mL, 9.2 mmol) and the reaction mixture was allowed to stir at room temperature for 2 h 15 min. The solvent was removed in vacuo, this was then repeated again with hexane (3×15 mL). The crude amine was then dried under high vacuum for 1 h 50 min. Then to a solution of PyBop (388.6 mg, 0.75 mmol) and Fmoc-D-Trp-OH (391.3 mg, 0.74 mmol) in CH$_2$Cl$_2$ (10 mL) was added diisopropylethylamine (0.315 mL, 1.8 mmol) under argon. A solution of the resultant deprotected amine in CH$_3$CN (10 mL) was added and the reaction was allowed to stir at room temperature for 16 h. The solvent was then removed in vacuo and the solid formed was purified by column chromatography on silica gel (eluent 3:7-1:1 EtOAc/

Hexane to give 2B (282 mg, 0.26 mmol, 50%) as a white solid: $R_f$ 0.52 EtOAc/Hexane (1:1); IR (thin film) 3308 (br), 1717 (m), 1651 (m), 1527 (br), 1450 (m).

Preparation of 3-[(R)-2-[(S)-1-((1R,2S)-3-allyloxy-carbonyl-2-hydroxy-1-isopropyl-propylcarbamoyl)-2-tritylsulfanyl-ethylcarbamoyl]-2-((E)-(S)-3-hydroxy-7-tritylsulfanyl-hept-4-enoylamino)-ethyl]-indole-1-carboxylic acid tert-butyl ester (4B)

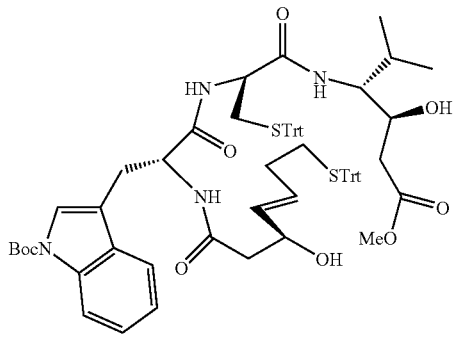

To a solution of 2B (279 mg, 0.26 mmol) in $CH_3CN$ (10.2 mL) was added diethylamine (0.41 mL, 3.9 mmol) under argon and was allowed to stir for 3 h. The solvent was then removed in vacuo and this was repeated with hexane (3×10 ml). Then to a solution of the crude amine in $CH_2Cl_2$ (5 mL) was added DMAP (4.1 mg, 0.033 mmol) followed by a solution of alcohol 3 (206 mg, 0.37 mmol) in $CH_2Cl_2$ (7 mL). The reaction was then stirred for 16 h. The solvent was then removed in vacuo and the solid formed was purified by column chromatography on silica gel (eluent 3:7-4:6-1:1 EtOAc/Hexane) to give 4B (189 mg, 0.15 mmol, 58%) as a white solid: $R_f$ 0.29 EtOAc/Hexane (1:1); IR (thin film) 3298 (br), 1731 (s), 1645 (s), 1593 (m), 1542 (m).

Preparation of 3-[(R)-2-[(S)-1-((1R,2S)-3-carboxy-2-hydroxy-1-isopropyl-propylcarbamoyl)-2-tritylsulfanyl-ethylcarbamoyl]-2-((E)-(S)-3-hydroxy-7-tritylsulfanyl-hept-4-enoylamino)-ethyl]-indole-1-carboxylic acid tert-butyl ester (5B)

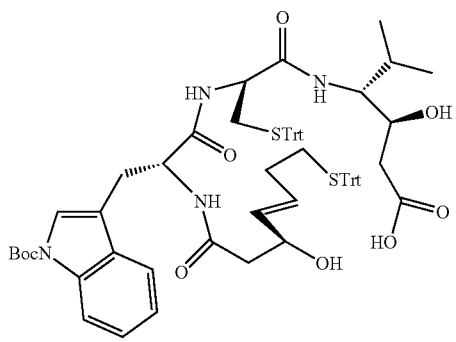

To a solution of 4B (166 mg, 0.13 mmol), $Pd(PPh_3)_4$ (15.7 mg, 0.014 mmol) in dry methanol (4 mL) under argon was added morpholine (24 μL, 0.27 mmol) which was allowed to stir for 1 h 20 min. The reaction mixture was concentrated in vacuo, $CH_2Cl_2$ (15 mL) was then added before washing with 1M HCl (10 mL), sat. sodium hydrogen carbonate (10 mL) and sat. brine (10 mL). The combined organic fractions were dried ($MgSO_4$), filtered and concentrated in vacuo. Purification by column chromatography on silica gel (eluent 5:95 MeOH/$CH_2Cl_2$ then +AcOH 1%) to give a white solid 5B (113 mg, 0.094 mmol, 70%): $R_f$ 0.19 MeOH/$CH_2Cl_2$ (5:95); IR (thin film) 3305 (br), 3292 (br), 1731 (s), 1649 (s), 1538 (s).

Preparation of 3-[(2S,6R,9S,12R,13S)-13-hydroxy-12-isopropyl-4,7,10,15-tetraoxo-2-((E)-4-tritylsulfanyl-but-1-enyl)-9-tritylsulfanylmethyl-1-oxa-5,8,11-triaza-cyclopentadec-6-ylmethyl]-indole-1-carboxylic acid tert-butyl ester (6B)

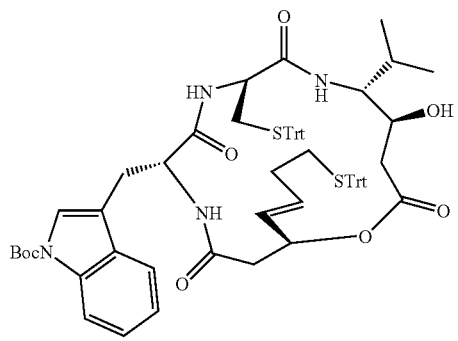

To a solution of MNBA (38 mg, 0.11 mmol) and DMAP (27 mg, 0.21 mmol) in $CH_2Cl_2$ (20 mL) was added dropwise a solution of acid 5B (113 mg, 0.094 mmol) in $CH_2Cl_2$ (82 mL) over 3 h. After a further 12 h the reaction mixture was washed with HCl (1M, 40 mL), sodium hydrogen carbonate (40 ml) and sat. brine (40 mL). The combined organic layers were dried ($MgSO_4$), filtered and concentrated in vacuo to give a brown solid. Purification by column chromatography on silica gel (eluent 4:6-1:1 EtOAc/Hexane increased to 1:9 MeOH/$CHCl_3$) which gave 6B (73.5 mg, 0.06 mmol, 55%) as a white/brown solid: $R_f$ 0.37 EtOAc/Hexane (1:1).

Preparation of 3-((E)-(1S,5S,6R,9 S,20R)-5-Hydroxy-6-isopropyl-3,8,18,21-tetraoxo-2-oxa-11,12-dithia-7,19,22-triaza-bicyclo[7.7.6]docos-15-en-20-ylmethyl)-indole-1-carboxylic acid tert-butyl ester (7B)

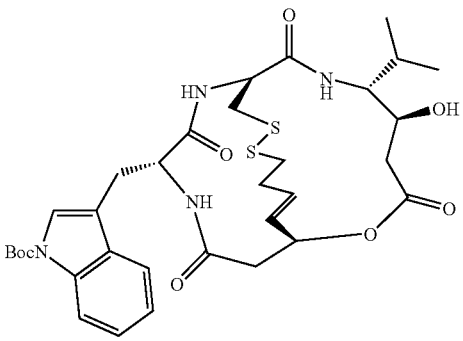

To a solution of iodine (107.2 mg, 0.42 mmol) in $CH_2Cl_2$/MeOH (9:1, 143 mL) was added dropwise a solution of 6B (48.4 mg, 0.0041 mmol) in CH$_2$Cl$_2$/MeOH (9:1) (70 mL) over 30 min, the reaction mixture was then allowed to stir for a further 30 min after which time sodium thiosulfate (26 mL, 0.05 M) was added. The organic phase was separated and the aqueous phase extracted with CH$_2$Cl$_2$ (3×20 mL). The combined organic phase was dried (MgSO$_4$), filtered and concentrated in vacuo. Purification by column chromatography on silica gel (eluent 0:100-1:99-3:97 MeOH/CH$_2$Cl$_2$) which gave 7B (13 mg, 0.019 mmol, 46%) as a white solid: R$_f$ 0.18 CH$_2$Cl$_2$/MeOH (97:3); [α]$^{28}_D$=−1.9 (c 0.36, CHCl$_3$); IR (thin film) 3379 (br), 3343 (br), 2974 (m), 2931 (m), 1732 (s), 1662 (s), 1538 (m), 1519 (m), 1453 (m), 1371 (s), 1333 (m), 1310 (m), 1271 (m), 1255 (s).

Preparation of (3S,4R)-4-{(S)-2-[(R)-2-(9H-fluoren-9-ylmethoxycarbonylamino)-4-methyl-pentanoylamino]-3-tritylsulfanyl-propionylamino}-3-hydroxy-5-methyl-hexanoic acid allyl ester (2C)

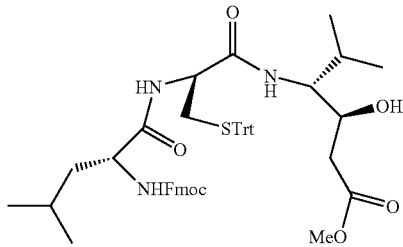

To a stirred solution of 1A (400 mg, 0.52 mmol) in CH$_3$CN (20 mL) at rt was added Et$_2$NH (1 mL) dropwise. The reaction mixture was stirred at rt for 2 h, whereupon the solvent was removed in vacuo, hexane (3×15 mL) was added and repeatedly removed in vacuo. The crude amine was then dried under high vacuum for 1 h. To a stirred solution of Fmoc-D-leu (265 mg, 0.75 mmol) in CH$_2$Cl$_2$ (10 mL) was added PyBop (390 mg, 0.75 mmol) and DIEA (217 µl, 1.25 mmol). After stirring at rt for 15 minutes a solution of the crude amine in CH$_3$CN (10 mL) was then added and the reaction mixture stirred for 12 h. Finally the solvent was removed and the residue was purified by flash chromatography (eluent 30-40% EtOAc/Hexane) to give 2C (260 mg, 0.295 mmol, 57%) as a white solid: [α]$^{27}$D+10.3 (c 0.50, CHCl$_3$).

Preparation of (3S,4R)-3-hydroxy-4-{(S)-2-[(R)-2-((E)-(R)-3-hydroxy-7-tritylsulfanyl-hept-4-enoylamino)-4-methyl-pentanoylamino]-3-tritylsulfanyl-propionylamino}-5-methyl-hexanoic acid allyl ester (4C)

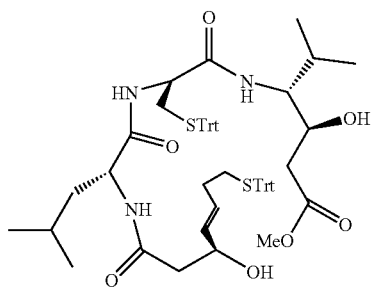

To a stirred solution of 2C (222 mg, 0.252 mmol) in CH$_3$CN (10 mL) at rt was added Et$_2$NH (461 µl) dropwise. After stirring for 3 h at rt the reaction mixture was concentrated in vacuo, hexane (3×15 mL) was added and repeatedly removed in vacuo giving the crude amine as a yellow oil. The crude amine was then dried under high vacuum for 1 h. Then to a solution of the crude amine in CH$_2$Cl$_2$ (5 mL) was added DMAP (3.2 mg, 0.026 mmol) followed by a solution of alcohol 3 (177 mg, 0.315 mmol) in CH$_2$Cl$_2$ (7 mL). The reaction was then stirred for 16 h. The solvent was then removed in vacuo and the solid formed was purified by column chromatography on silica gel (eluent 30-50% EtOAc/Hexane) to give 4C (180 mg, 0.17 mmol, 67%) as a white solid: [α]$^{25}$D+19.47 (c 0.48, CH$_3$OH).

Preparation of (3S,4R)-3-Hydroxy-4-{(S)-2-[(R)-2-((E)-(R)-3-hydroxy-7-tritylsulfanyl-hept-4-enoylamino)-4-methyl-pentanoylamino]-3-tritylsulfanyl-propionylamino}-5-methyl-hexanoic acid (5C)

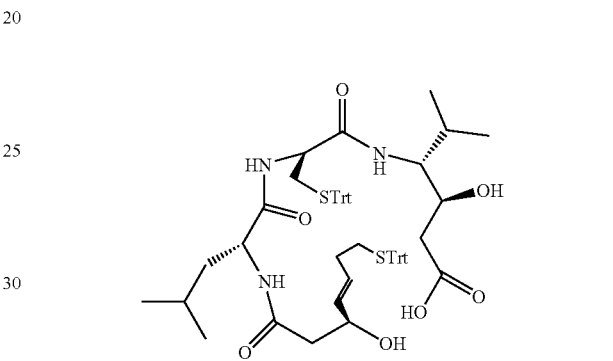

To a solution of 4C (168 mg, 0.158 mmol) in dry CH$_3$OH (5 mL) at rt was added morpholine (27.6 µl, 0.48 mmol) followed by Pd(PPh$_3$)$_4$ (18.3 mg, 0.016 mmol). After stirring for 2 h the solvent was evaporated, the product rinsed with CH$_2$Cl$_2$ and washed with 1 M HCl (10 mL), sat NaHCO$_3$ (10 mL) and sat. NaCl (10 mL) solutions. The organic layer was then dried with MgSO$_4$ and filtered, the solvent was removed in vacuo and the crude product was washed with hexane (3×20 mL) and purified by flash chromatography (1-20% CH$_3$OH/CHCl$_3$) to give 5C (101 mg, 0.1 mmol, 63%).

Preparation of (2S,6R,9 S,12R,13R)-13-Hydroxy-6-isobutyl-12-isopropyl-2-((E)-4-tritylsulfanyl-but-1-enyl)-9-tritylsulfanylmethyl-1-oxa-5,8,11-triaza-cyclopentadecane-4,7,10,15-tetraone (6C)

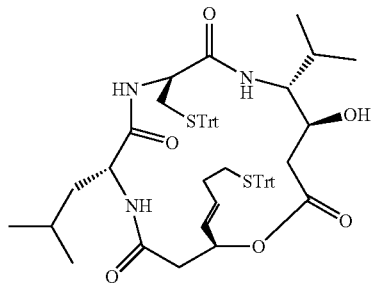

To a solution of 2-methyl-6-nitrobenzoic anhydride (MNBA) (32.7 mg, 0.095 mmol) and DMAP (22.5 mg, 0.184 mmol) in CH$_2$Cl$_2$ (20 mL) was added dropwise a solution of acid 5C (76 mg, 0.075 mmol) in CH$_2$Cl$_2$/THF (2:1, 66 mL) over 3 hours. After a further 12 h the reaction was quenched by the addition of 1M HCl (30 mL). The organic phase was separated (extracting with CH$_2$Cl$_2$) and washed with sat NaHCO$_3$ (30 mL), followed by brine (30 mL). The combined organic phase was dried (MgSO$_4$), filtered and concentrated in vacuo to give a yellow oil. Purification by column chromatography on silica gel (eluent 40% EtOAc/Hexane) gave 6C (35 mg, 0.035 mmol, 47%) as a yellow oil.

Preparation of (E)-(1S,5R,6R,9S,20R)-5-Hydroxy-20-isobutyl-6-isopropyl-2-oxa-11,12-dithia-7,19,22-triaza-bicyclo[7.7.6]docos-15-ene-3,8,18,21-tetraone (7C)

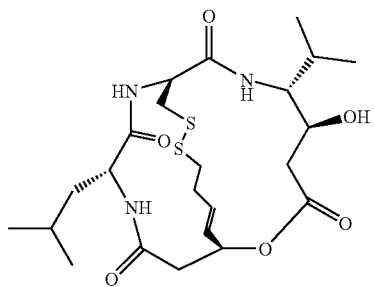

To a solution of 12 (81.2 mg, 0.32 mmol) in CH$_2$Cl$_2$/MeOH (9:1, 120 mL) was added dropwise a solution of 6C (32 mg, 0.032 mmol) in CH$_2$Cl$_2$/MeOH (9:1, 70 mL) over 30 min. After a further 30 min the reaction was quenched by the addition of sodium thiosulfate (0.05M, 50 mL) and Brine (10 mL). The organic phase was separated and the aqueous phase extracted with CH$_2$Cl$_2$ (3×20 mL). The combined organic phase was dried (MgSO$_4$), filtered and concentrated in vacuo giving a yellow oil. Purification by column chromatography on silica gel (1-3% MeOH/CH$_2$Cl$_2$) gave cyclised depsipeptide 7C (13.5 mg, 0.026 mmol, 82%): [α]$^{29}_D$ −66.6 (c 0.5, CH$_3$OH).

Preparation of (3S,4R)-4-[(S)-2-(9H-fluoren-9-yl-methoxycarbonylamino)-3-tritylsulfanyl-propionylamino]-3-hydroxy-5-phenyl-pentanoic acid allyl ester (1B)

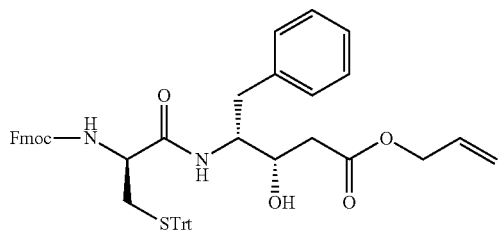

1) Preparation of (R)-4-tert-butoxycarbonylamino-3-oxo-5-phenyl-pentanoic acid allyl ester

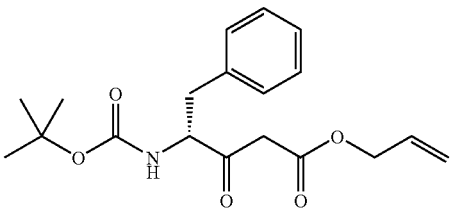

To a solution of Boc-D-Phe-OH (2.53 g, 9.4 mmol) in CH$_2$Cl$_2$ (50 mL) at 0° C. was added EDAC.HCl (2.25 g, 11.3 mmol), pentafluorophenol (1.80 g, 9.9 mmol) and DMAP (0.23 g, 1.9 mmol). After stirring for 30 minutes the solution was warmed to rt and left for a further 2 h. The reaction mixture was then washed with 10% HCl (40 mL), sat. NaHCO$_3$ (25 mL) and sat NaCl (25 mL) solutions, extracting with CH$_2$Cl$_2$. The combined organic layers were dried (Na$_2$SO$_4$), filtered, and concentrated to give the activated ester as an off white solid. Meanwhile, to a solution of DIPEA (3.25 mL, 23.2 mmol) in THF (30 mL) at −40° C. was added dropwise a solution of nBuLi in hexane (1.6 M, 14.5 mL, 23.2 mmol). The reaction mixture was warmed to 0° C. over 10 min whereupon it was then cooled to −78° C. and allyl acetate (2.5 mL, 23.2 mmol) added dropwise. After 30 min a solution of the activated ester in THF (20 mL) was added dropwise. After a further 1 h the reaction mixture was washed sequentially with 10% HCl (40 mL), sat. NaHCO$_3$ (25 mL) and sat NaCl (25 mL) solutions, extracting with CH$_2$Cl$_2$. The combined organic layers were dried (Na$_2$SO$_4$), filtered, and concentrated. Purification by column chromatography on silica gel (20% EtOAc/Hex) gave the β-keto ester (1.66 g, 4.8 mmol, 51%).

2) Preparation of (3S,4R)-4-tert-butoxycarbonylamino-3-hydroxy-5-phenyl-pentanoic acid allyl ester

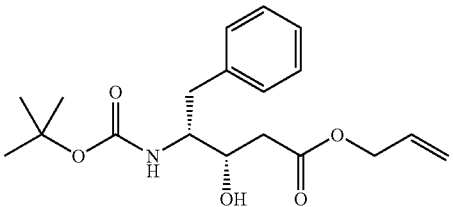

To a solution of the β-keto ester (1.47 g, 4.23 mmol) in MeOH (60 mL) at −78° C. was added in one batch KBH$_4$ (0.8 g, 14.82 mmol). After 10 min the reaction was warmed to −20° C. over 30 min. After a further 10 min the reaction was brought to 0° C. and quenched by the addition of AcOH until pH 7. The reaction mixture was concentrated in vacuo, EtOAc (40 mL) was added before washing with sat NaCl (25 mL) solution, drying (MgSO$_4$), and concentrating in vacuo. Purification by column chromatography on silica gel (20% EtOAc/Hex) gave the β-hydroxy ester (0.99 g, 2.85 mmol, 67%).

3) To a solution of the amide (0.52 g, 1.5 mmol) in CH$_2$Cl$_2$ (20 mL) at 0° C. was added TFA (5 mL). After 1.5 h the mixture was concentrated in vacuo. To a suspension of Fmoc-D-Cys(Trt)-OH (0.92, 1.57 mmol) in CH$_2$Cl$_2$ (60 mL) at 0° C. was added PyBOP (0.94 g, 1.8 mmol) and DIEA (0.91 mL, 5.25 mmol). After 5 min a solution of the amine salt (prepared above) in CH$_2$Cl$_2$ (10 mL) was added. After a further 1 h the reaction mixture was concentrated in vacuo. Purification by column chromatography on silica gel (20-35% EtOAc/Hex) gave 1B (1.02 g, 1.2 mmol, 83%).

Preparation of (3S,4R)-4{(S)-2-[(R)-2-(9H-fluoren-9-ylmethoxycarbonylamino)-propionylamino]-3-tritylsulfanyl-propionylamino}-3-hydroxy-5-phenyl-pentanoic acid allyl ester (2D)

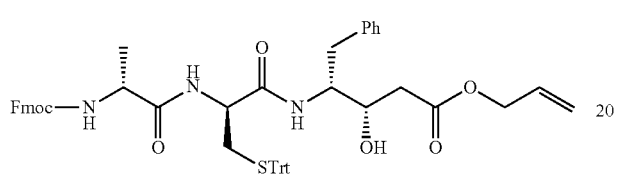

To a solution of 10 (400 mg, 0.5 mmol) in CH$_3$CN (25 mL) was added Et$_2$NH (1.2 mL, 5% v/v). After 1 h the reaction mixture was concentrated in vacuo to give the crude amine. Hexane (100 mL) was then added to the reaction mixture and the solvent was removed in vacuo, this was repeated again with hexane (2×25 mL). The crude amine was then dried under high vacuum for 0.5 h. Then to a solution of PyBop (380 mg, 0.73 mmol) and Fmoc-D-Ala-OH (220 mg, 0.70 mmol) in CH$_3$CN/CH$_2$Cl$_2$ (1:1, 20 mL) at 0° C. was added DIEA (0.3 mL, 3.5 mmol) under argon. A solution of the crude amine in CH$_3$CN/CH$_2$Cl$_2$ (1:1, 10 mL) was added and the reaction mixture brought to rt and stirred for 1.5 h. The solvent was then removed in vacuo. Purification by column chromatography on silica gel (50% EtOAc/Hex) gave 2D (360 mg, 0.41 mmol, 84%).

Preparation of (3S,4R)-3-hydroxy-4{(S)-2-[(R)-2-((E)-(S)-3-hydroxy-7-tritylsulfanyl-hept-4-enoy-lamino)-propionylamino]-3-tritylsulfanyl-propiony-lamino}-5-phenyl-pentanoic acid allyl ester (4D)

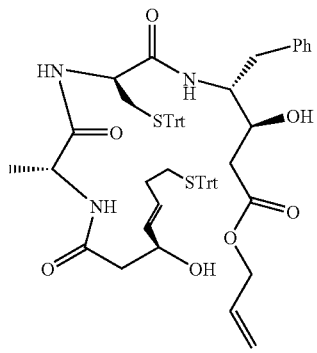

To a stirred solution of 2D (325 mg, 0.36 mmol) in CH$_2$Cl$_2$/CH$_3$CN (1:1, 10 mL) at rt was added Et$_2$NH (0.7 mL). After stirring for 4 h, hexane (20 mL) was added to the reaction mixture and then the solvent was removed in vacuo, this was repeated again with hexane (2×25 mL). The crude amine was then dried under high vacuum for 0.5 h. To a stirred solution of the crude amine in CH$_2$Cl$_2$/CH$_3$CN (1:1, 10 mL) was added a solution of 3 (250 mg, 0.44 mmol) in CH$_2$Cl$_2$ (5 mL) and DMAP (5 mg, 0.04 mmol) at rt. After stirring at rt for 12 hours, the solvent was removed in vacuo and the residue was purified by flash chromatography (eluent 25-35% EtOAc/CH$_2$Cl$_2$) to give 4D (278 mg, 72%).

Preparation of (3S,4R)-3-hydroxy-4{(S)-2-[(R)-2-((E)-(S)-3-hydroxy-7-tritylsulfanyl-hept-4-enoy-lamino)-propionylamino]-3-tritylsulfanyl-propiony-lamino}-5-phenyl-pentanoic acid (5D)

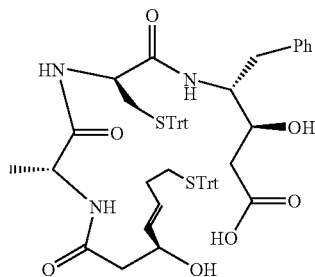

To a solution of 4D (170 mg, 0.159 mmol), Pd(PPh$_3$)$_4$ (9 mg, 0.008 mmol) in dry methanol (6 mL) under argon was added morpholine (28 µL, 0.32 mmol) which was allowed to stir for 3 h. The reaction mixture was concentrated in vacuo, CH$_2$Cl$_2$ (20 mL) was then added before washing with 1M HCl (15 mL), sat. sodium hydrogen carbonate (15 mL), sat. brine (15 mL), dried over MgSO$_4$ and concentrated in vacuo. Purification was then carried out by column chromatography on silica gel (5-8% MeOH/CH$_2$Cl$_2$ then +0.2% AcOH) to give 5D (130 mg, 0.13 mmol, 61%).

Preparation of (2S,6R,9S,12R,13S)-12-benzyl-13-hydroxy-6-methyl-2-((E)-4-tritylsulfanyl-but-1-enyl)-9-tritylsulfanylmethyl-1-oxa-5,8,11-triaza-cyclopentadecane-4,7,10,15-tetraone (6D)

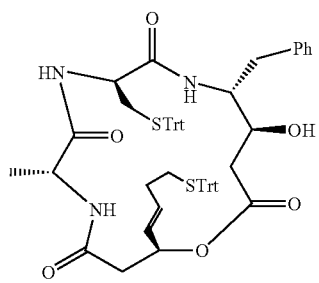

To a solution of MNBA (39 mg, 0.11 mmol) and DMAP (28 mg, 0.23 mmol) in CH$_2$Cl$_2$ (20 mL) was added dropwise a solution of acid 5D (98 mg, 0.095 mmol) in CH$_2$Cl$_2$ (90 mL) over 3 h. After a further 12 h the reaction mixture was washed with HCl (1M, 40 mL), sodium hydrogen carbonate (40 ml) and sat. brine (40 mL). The combined organic layers were dried over MgSO$_4$ and concentrated in vacuo to give a brown solid. Purification by column chromatography on silica gel (30-60 EtOAc/Hexane) which gave 6D (42 mg, 0.04 mmol, 42%).

Preparation of (E)-(1S,5S,6R,9S,20R)-6-Benzyl-5-hydroxy-20-methyl-2-oxa-11,12-dithia-7,19,22-triaza-bicyclo[7.7.6]docos-15-ene-3,8,18,21-tetraone (7D) & isomer (7D'), ratio 1:1)

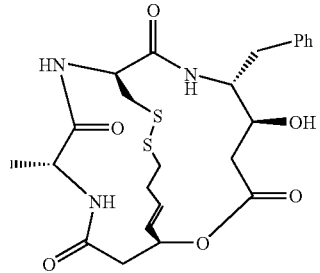

To a stirred solution of iodine (99 mg, 0.39 mmol) in $CH_2Cl_2$/MeOH (9:1, 110 mL) was added dropwise a solution of 6D (40 mg, 0.0039 mmol) in $CH_2Cl_2$/MeOH (9:1, 60 mL) over 30 min, the reaction mixture was then allowed to stir for a further 30 min after which time sodium thiosulfate (40 mL, 0.05 M) was added. The layers were separated and the product was extracted with $CH_2Cl_2$ (3×25 ml) dried over $MgSO_4$ and the solvent was removed in vacuo. Purification was then carried out by column chromatography on silica gel (1-5% MeOH/$CH_2Cl_2$) which gave an inseparable mixture of isomers 7D & 7D' (1:1, 11 mg, 0.02 mmol, 54%).

Preparation of (3S,4R)-4{(S)-2-[(R)-2-(9H-fluoren-9-ylmethoxycarbonylamino)-3-phenyl-propionylamino]-3-tritylsulfanyl-propionylamino}-3-hydroxy-5-phenyl-pentanoic acid allyl ester (2E)

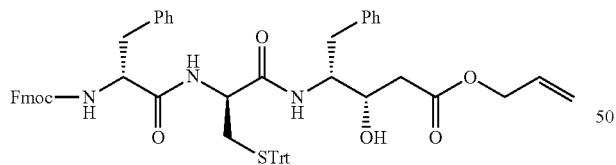

To a solution of 1B (390 mg, 0.48 mmol) in $CH_3CN$ (20 mL) was added $Et_2NH$ (1 mL, 5% v/v). After 1 h the reaction mixture was concentrated in vacuo to give the crude amine. Hexane (100 mL) was then added to the reaction mixture and the solvent was removed in vacuo, this was repeated again with hexane (2×25 mL). The crude amine was then dried under high vacuum for 0.5 h. Then to a solution of PyBop (360 mg, 0.69 mmol) and Fmoc-D-Phe-OH (260 mg, 0.67 mmol) in $CH_3CN/CH_2Cl_2$ (1:1, 20 mL) at 0° C. was added DIEA (0.3 mL, 3.5 mmol) under argon. A solution of the crude amine in $CH_3CN/CH_2Cl_2$ (1:1, 10 mL) was added and the reaction mixture brought to rt and stirred for 1.5 h. The solvent was then removed in vacuo. Purification by column chromatography on silica gel (20-40% EtOAc/Hex) gave 2E (405 mg, 0.43 mmol, 90%).

Preparation of (3S,4R)-3-hydroxy-4{(S)-2-[(R)-2-((E)-(S)-3-hydroxy-7-tritylsulfanyl-hept-4-enoylamino)-3-phenyl-propionylamino]-3-tritylsulfanyl-propionylamino}-5-phenyl-pentanoic acid allyl ester (4E)

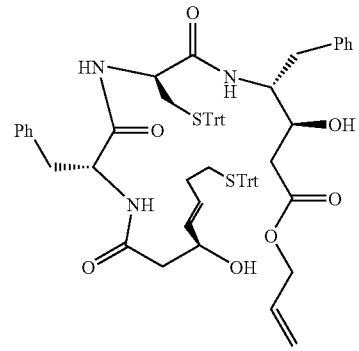

To a stirred solution of 2E (360 mg, 0.37 mmol) in $CH_2Cl_2$/$CH_3CN$ (1:1, 15 mL) at rt was added $Et_2NH$ (0.7 mL). After stirring for 4 h, hexane (20 mL) was added to the reaction mixture and then the solvent was removed in vacuo, this was repeated again with hexane (2×25 mL). The crude amine was then dried under high vacuum for 0.5 h. To a stirred solution of the crude amine in $CH_2Cl_2/CH_3CN$ (1:1, 10 mL) was added a solution of 3 (270 mg, 0.48 mmol) in $CH_2Cl_2$ (5 mL) and DMAP (5 mg, 0.04 mmol) at rt. After stirring at rt for 12 hours, the solvent was removed in vacuo and the residue was purified by flash chromatography (eluent 20-35% EtOAc/$CH_2Cl_2$) to give 4E (210 mg, 68%).

Preparation of (3S,4R)-3-hydroxy-4{(S)-2-[(R)-2-((E)-(S)-3-hydroxy-7-tritylsulfanyl-hept-4-enoylamino)-3-phenyl-propionylamino]-3-tritylsulfanyl-propionylamino}-5-phenyl-pentanoic acid (5E)

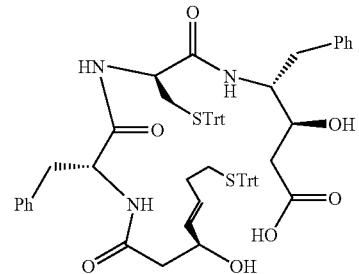

To a solution of 4E (210 mg, 0.184 mmol), $Pd(PPh_3)_4$ (21 mg, 0.018 mmol) in dry methanol/$CH_2Cl_2$ (5:1, 6 mL) under argon was added morpholine (32 μL, 0.37 mmol) which was allowed to stir for 3 h. The reaction mixture was concentrated in vacuo, $CH_2Cl_2$ (20 mL) was then added before washing with 1M HCl (15 mL), sat. sodium hydrogen carbonate (15 mL), sat. brine (15 mL), dried over $MgSO_4$ and concentrated in vacuo. Purification was then carried out by column chromatography on silica gel (6-10% MeOH/$CH_2Cl_2$) to give 5E (140 mg, 0.13 mmol, 69%).

Preparation of (2S,6R,9S,12R,13S)-6,12-dibenzyl-13-hydroxy-2-((E)-4-tritylsulfanyl-but-1-enyl)-9-tritylsulfanyl methyl-1-oxa-5,8,11-triaza-cyclopentadecane-4,7,10,15-tetraone (6E)

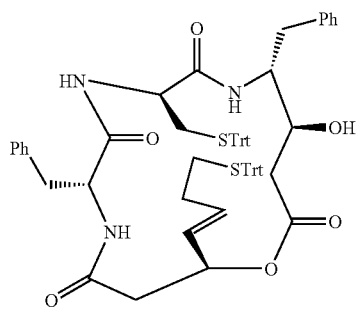

To a solution of MNBA (45 mg, 0.12 mmol) and DMAP (32 mg, 0.26 mmol) in $CH_2Cl_2$ (30 mL) was added dropwise a solution of acid 5E (120 mg, 0.11 mmol) in $CH_2Cl_2$ (120 mL) over 3 h. After a further 12 h the reaction mixture was washed with HCl (1M, 40 mL), sodium hydrogen carbonate (40 ml) and sat. brine (40 mL). The combined organic layers were dried over $MgSO_4$ and concentrated in vacuo to give a brown solid. Purification by column chromatography on silica gel (30-50 EtOAc/Hexane) which gave 6E (45 mg, 0.04 mmol, 38%).

Preparation of (E)-(1S,5S,6R,9S,20R)-6,20-dibenzyl-5-hydroxy-2-oxa-11,12-dithia-7,19,22-triaza-bicyclo[7.7.6]docos-15-ene-3,8,18,21-tetraone (7E)

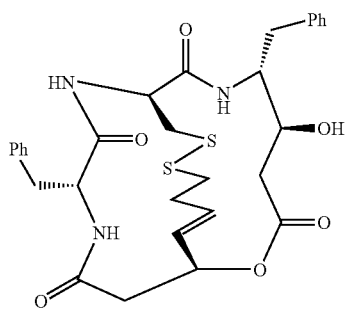

To a stirred solution of iodine (71 mg, 0.28 mmol) in $CH_2Cl_2$/MeOH (9:1, 120 mL) was added dropwise a solution of 6E (30 mg, 0.0028 mmol) in $CH_2Cl_2$/MeOH (9:1, 70 mL) over 30 min, the reaction mixture was then allowed to stir for a further 30 min after which time sodium thiosulfate (40 mL, 0.05 M) was added. The layers were separated and the aqueous was extracted with $CH_2Cl_2$ (3×25 ml). The combined organic phase was dried over $MgSO_4$, filtered and the solvent removed in vacuo. Purification by column chromatography on silica gel (0.5-4% MeOH/$CH_2Cl_2$) gave 7E (15 mg, 0.025, 90%): $[\alpha]^{26}_D = -0.1$ (CHCl_3, C 0.53).

Further compounds of the invention are shown in Table 1. They were prepared by the same general procedures as exemplified above, making appropriate changes that will be apparent to one of ordinary skill in the art.

TABLE 1

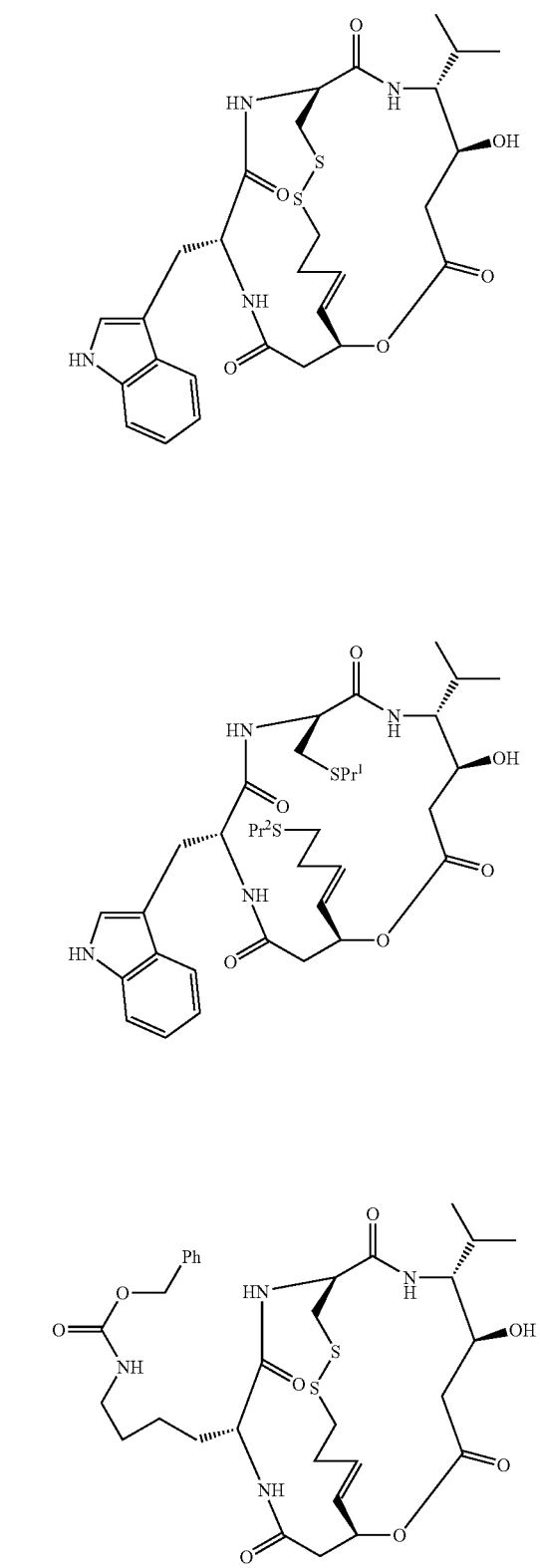

TABLE 1-continued
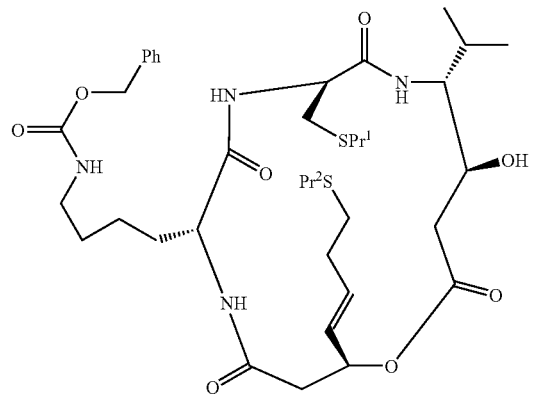
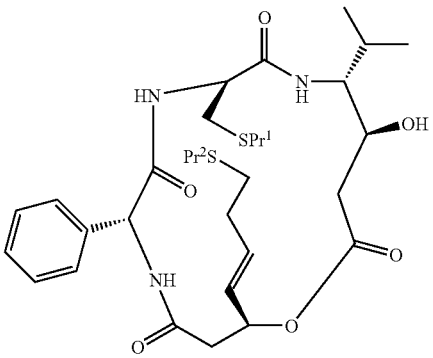
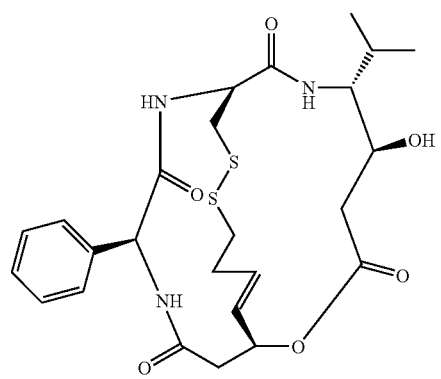
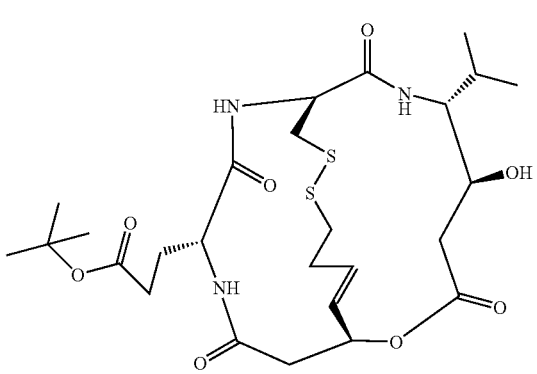
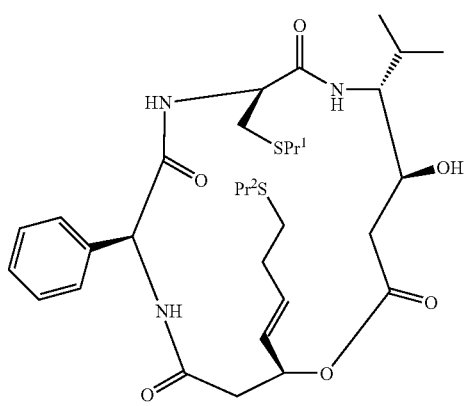
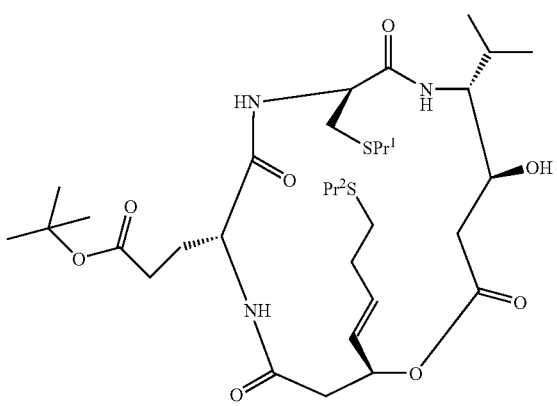
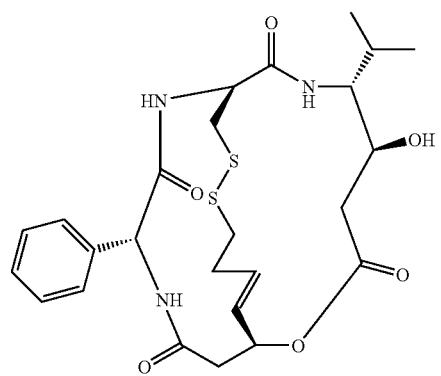
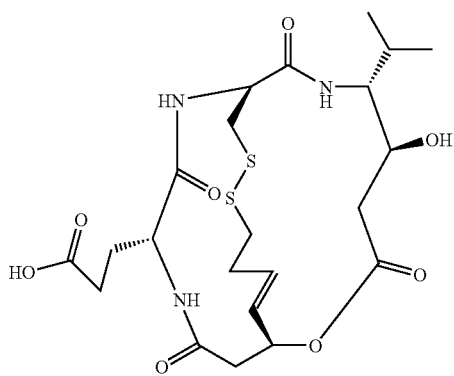

TABLE 1-continued
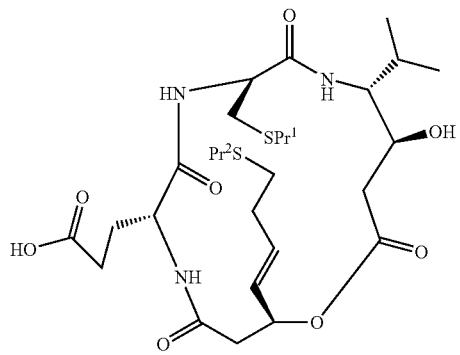
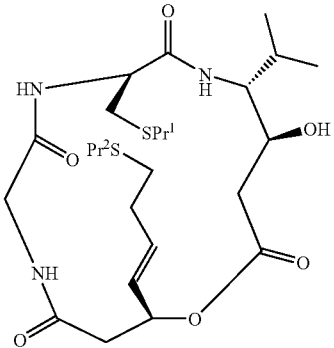
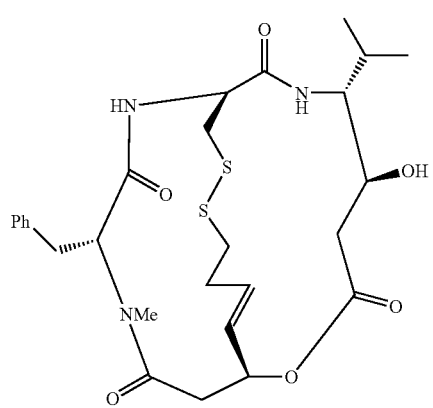
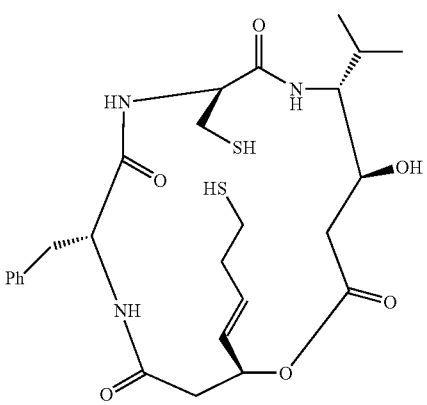
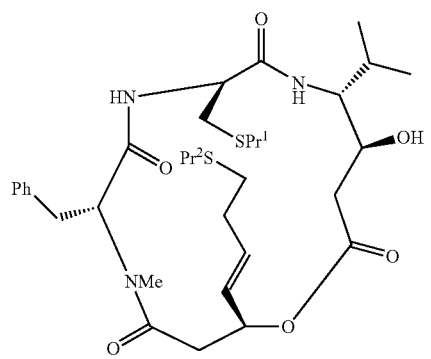
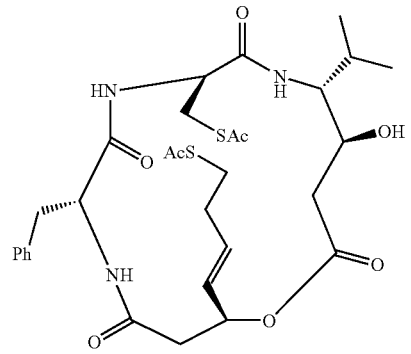
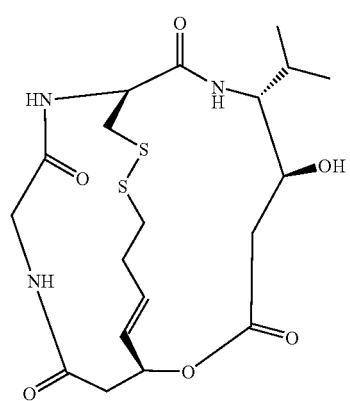
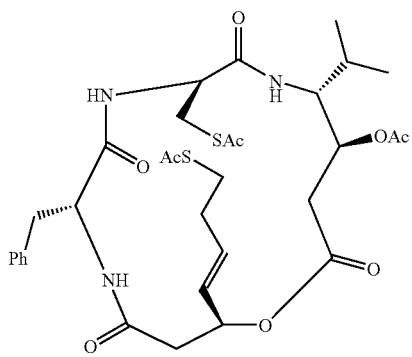

TABLE 1-continued

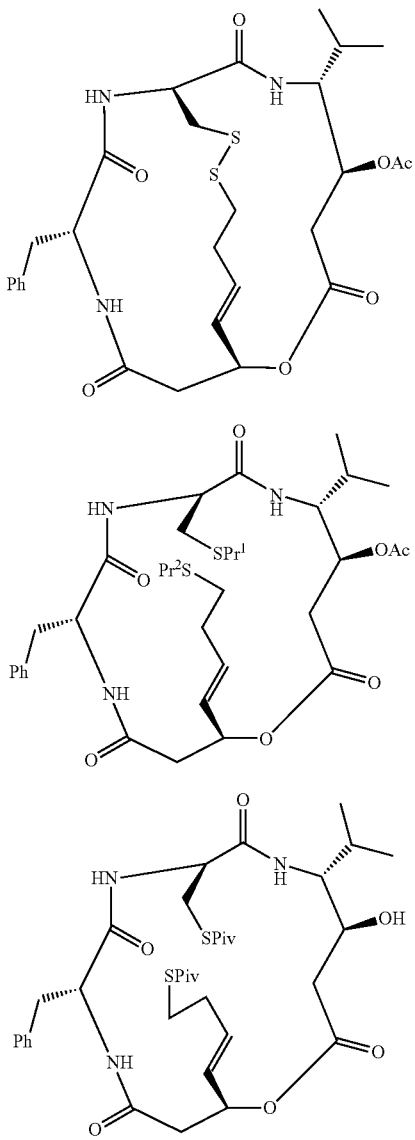

Activity Assay 1

In vitro HDAC assays were performed using a HDAC fluorescent activity assay kit (Biomol, UK) according to the manufacturer's instructions. Compounds were reduced prior to analysis; 1 mM compound was reduced with 30 mM DTT in DMSO overnight at room temperature, protected from light. Reactions were then set up in a 96-well plate. For each reaction 10 µl compound (5× required concentration in assay buffer) was mixed with 15 µl diluted Hela Nuclear Extract (30-fold in assay buffer). Serial dilutions were set up for each compound. Reactions containing Hela extract only and assay buffer only were also set up. 25 µl diluted Fluor de LYS™ substrate (100-fold in assay buffer) was added to each reaction, which were then incubated at 37° C. for 1 hour. The reaction was stopped by addition of 50 µl Fluor de LYS™ Developer (20-fold dilution in assay buffer, plus TSA diluted 100-fold). The reactions were then incubated at room temperature for 10 minutes before fluorescence was measured using a CytoFluor II Fluorescence Multiwell Plate Reader and CytoFluor II software with filters set at 360 nM for excitation and 460 nM for emission. Inhibition of in vitro HDAC activity was determined for mean values of duplicate samples as percentages relative to HeLa extract only reactions. $IC_{50}$ values were calculated using GraphPad Prism software. Results are shown In Table 2 (structures shown above).

TABLE 2

| Inhibition of HDAC activity | |
|---|---|
| Compound | $IC_{50}$ (nM) |
| SAHA | 330 |
| Compound 7A | 3.3 |
| Compound 7B | 436 |
| Compound 7C | 11 |
| Compound 7D | 18 |
| Compound 7E | 30 |

Activity Assay 2

Cell proliferation assays were performed using the CyQuant™ assay system (Molecular Probes, Inc. USA) according to the manufacturer's instructions. MCF7 breast, A2780 ovarian and PC3 and LNCAP prostate cancer cells were plated in 96 well plates, at a density of 1000 cells for MCF7 cells or 5000 cells for A2780/PC3/LNCAP cells, in 100 µl of cell culture medium per well. Compounds were added a minimum of 5 hours later, in serial dilutions in cell culture medium, in 100 µl volumes at 2× final concentration. Cell culture medium was removed after 4 (A2780, PC3 or LNCAP cells) or 6 days (MCF7 cells) by inversion of the plate onto blotting paper and cells were gently washed once with 200 µl PBS. Plates were frozen immediately for a minimum of one hour at −80° C. and then thawed. 200 µl of 1× CyQuant cell lysis buffer supplemented with dye, made according to the manufacturer's instruction, was added immediately to each well and incubated at room temperature for 3-5 minutes. Fluorescence was then measured for each well using a Cytofluor II Fluoresence Multiwell Plate Reader and CytoFluor II software with filters at 480 nm for excitation and 520 nm for emission maxima. Cell proliferation was determined for mean values of duplicate samples as percentages relative to untreated cell samples (=100%). $IC_{50}$ values were calculated using GraphPad Prism software, and the results are shown in Table 3 (structures shown above).

TABLE 3

| Cell growth inhibition ($IC_{50}$ values (nM)) | |
|---|---|
| Compound | $IC_{50}$ (nM) |
| SAHA | 483 |
| Compound 7A | 0.07 |
| Compound 7B | 0.65 |
| Compound 7C | 0.23 |
| Compound 7D | 55 |
| Compound 7E | 3.2 |

Activity Assay 3

TNF-α immunoassays were carried out using the Quantikine® Human TNF-α assay kit (R&D systems, Abingdon UK) according to the manufacturer's instructions. Human whole blood was separated using Ficol Paque™ Plus (GE Healthcare, Amersham, UK) and the PBMCs were plated in 24 well plates, at a density of $2.5 \times 10^6$ in 500 µl of cell culture medium per well. Compounds were added 1 hour later in volumes of 100 µl at 6× final concentration. Five hours later, lipopolysaccharide (LSP, Sigma, Poole, UK) was added in a volume of 10 µl at 60× final concentration plates were mixed and left overnight at 37° C. 5% $CO_2$. Plates were centrifuged and cell supernatant was transferred to a new plate. The Quantikine® assay reagents and standards were prepared according to the manufacturer instructions. The Quantikine® assay plate was prepared by adding 50 μl of assay diluent RD1F into each well. This was followed by 200 μl of standard or 100 μl of calibrator diluent plus 100 μl cell supernatant; this was incubated for 2 hours at room temperature (RT). The plate was washed using wash buffer 4 times. After the final wash the plate was tapped on clean paper towel to remove all residual buffer. 200 μl of TNF-α conjugate was added to each well and incubated for 1 hour at RT. The plate was then washed as before. The required amount of substrate solution was prepared by adding equal volumes of colour reagents A and B, protecting from light, 200 μl of this mix was added to each well and incubated for 20 mins at RT, protected from light. 50 μl of stop solution was added to each well in the same order as the substrate solution and the plate was read on a Biorad 680 96 well plate reader (Bio-Rad, Hemel Hempstead, UK) at 450 nm with λ correction at 570 nm. TNF-α levels were determined for mean values of duplicate samples using absorbance in nm, calibration zero values were subtracted from all results to correct for the addition of calibrator diluent in the assay. Results are shown in Table 4.

TABLE 4

| Group | TNFα Secretion (Normalized*) | Standard Deviation (Normalized*) |
|---|---|---|
| Untreated cells | 0.03 | 0.00 |
| Cells + 10 pg LPS | 100.00 | 9.95 |
| Cells + 0.4 nM Compound 7A | 0.13 | 0.46 |
| Cells + 10 pg LPS + 0.4 nM Compound 7A | 18.66 | 8.49 |
| Cells + 0.2 nM Compound 7A | −0.03 | 0.05 |
| Cells + 10 pg LPS + 0.2 nM Compound 7A | 31.11 | 0.64 |
| Cells + 0.1 nM Compound 7A | −0.08 | 0.02 |
| Cells + 10 pg LPS + 0.1 nM Compound 7A | 45.45 | 3.53 |
| Cells + 0.05 nM Compound 7A | −0.06 | 0.46 |
| Cells + 10 pg LPS + 0.05 nM Compound 7A | 58.12 | 1.68 |
| Cells + 0.025 nM Compound 7A | −0.26 | −0.05 |
| Cells + 10 pg LPS + 0.025 nM Compound 7A | 63.90 | 16.01 |

*TNFα secretion measured at 450 nM with λ correction at 570 nM. Absorbances are normalized to value for cells treated with 10 pg LPS alone (=100.00)

The invention claimed is:

1. A Spiruchostatin analogue of formula (I) or (I')

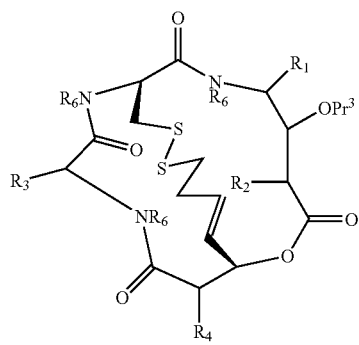

(I)

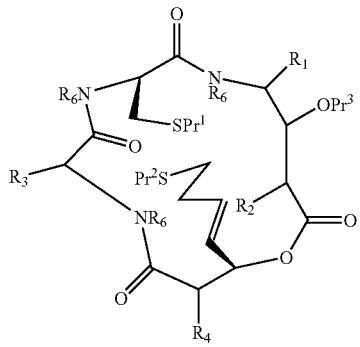

(I')

including isosteres and pharmaceutically acceptable salts thereof;
wherein
$R_1$, $R_2$ and $R_4$, are the same or different and each is selected from —H, —$C_1$-$C_6$ alkyl, —$C_2$-$C_6$ alkenyl, -L-O—C(O)—R', -LC(O)—O—R', -L-A, -L-NR"R", -L-Het-C(O)-Het-R" and -L-Het-R", wherein L is a $C_1$-$C_6$ alkylene group, A is phenyl or a 5- to 6-membered heteroaryl group, each R' is the same or different and represents $C_1$, -$C_4$ alkyl, each R" is the same or different and represents H or $C_1$-$C_6$ alkyl, each -Het- is the same or different and is a heteroatom spacer selected from —O—, -N(R''')— and —S—and each R''' is the same or different and represents H or $C_1$-$C_4$ alkyl;
$R_3$ is selected from —($C_1$-$C_4$alkyl)-A", —$C_4$-$C_6$ alkenyl, -L-O—C(O)—R', -L-C(O)—O—R", -L-A, -L-NR"R", -L-Het-C(O)-Het-R" and -L-Het- R", wherein A"is a $C_6$-$C_{10}$ aryl group or a 5- to 10-membered heteroaryl group and A, L, R', R", R''' and Het are as defined above;
each $R_6$ is the same or different and represents hydrogen or $C_1$-$C_4$ alkyl; and
$Pr^1$, $Pr^2$ and $Pr^3$ are each hydrogen.

2. The analogue according to claim 1, wherein in the compound of formula (I') $R_1$, $R_2$, $R_3$, $R_4$ and $R_6$ are not all the same.

3. The analogue according to claim 1, of formula (I).

4. The analogue according to claim 1, wherein $R_1$, $R_2$, $R_3$ and $R_4$ are the same or different and each is selected from —H, —$C_1$-$C_6$ alkyl, —$C_2$-$C_6$ alkenyl, -L-O—C(O)—R', -L-C(O)—O—R", -L-A, -L-NR"R", -L-Het-C(O)-Het-R" and -L-Het-R", wherein L is a $C_1$-$C_6$ alkylene group, A is phenyl or a 5- to 6-membered heteroaryl group, each R' is the same or different and represents $C_1$-$C_4$ alkyl, each R" is the same or different and represents H or $C_1$-$C_6$ alkyl, each -Het- is the same or different and is a heteroatom spacer selected from —O—, —N(R''')—and —S—, and each R''' is the same or different and represents H or $C_1$-$C_4$ alkyl.

5. The analogue according to claim 1, wherein A is phenyl.

6. The analogue according to claim 1, wherein -Het- is —O— or -NR'''.

7. The analogue according to claim 1, wherein $R_1$ is selected from —H and —$C_1$-$C_6$ alkyl.

8. The analogue according to claim 1, wherein $R_3$ is selected from -L-C (O)—O—R", -L-A, -L-NR"R" and -L-N(R")—C(O)—O—R".

9. The analogue according to claim 1, wherein $R_2$ is selected from —H and —$C_1$-$C_4$ alkyl.

10. The analogue according to claim 1, wherein $R_4$ is selected from —H and —$C_1$-$C_4$ alkyl.

11. The analogue according to claim 1, wherein $R_6$ is —H.

12. The analogue according to claim 1, which is a compound of formula (2), (2'), (3), (3'), (5), (5'), (7), (7'), (8), (8'), (9), (9'), (9"), (9'"), (10), (10'), (11), (11'), (12), (12'), (14), (14'"), or (14"")
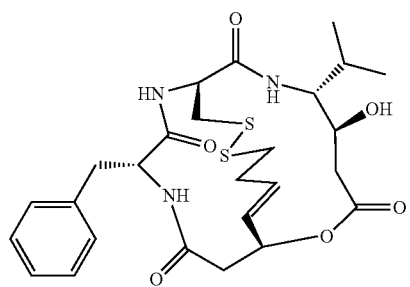
(2)
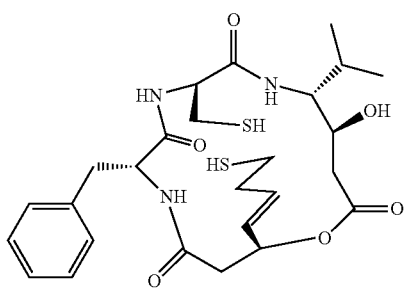
(2')
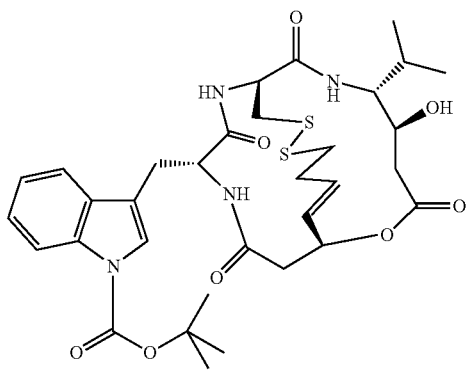
(3)
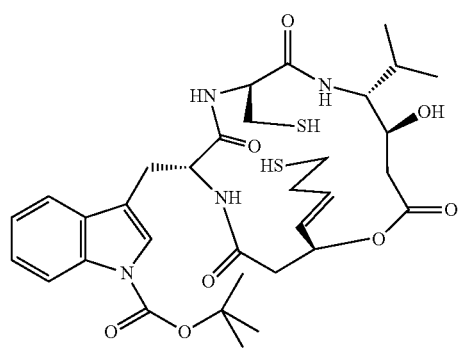
(3')
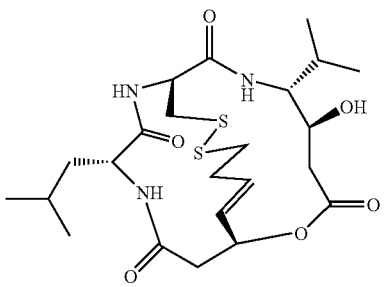
(4)
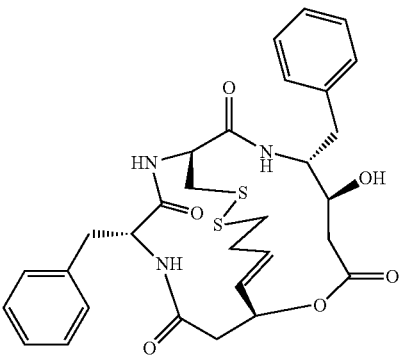
(5)
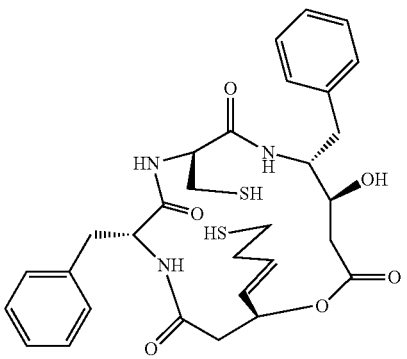
(5')
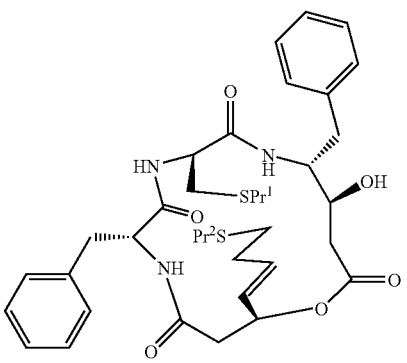
(5')

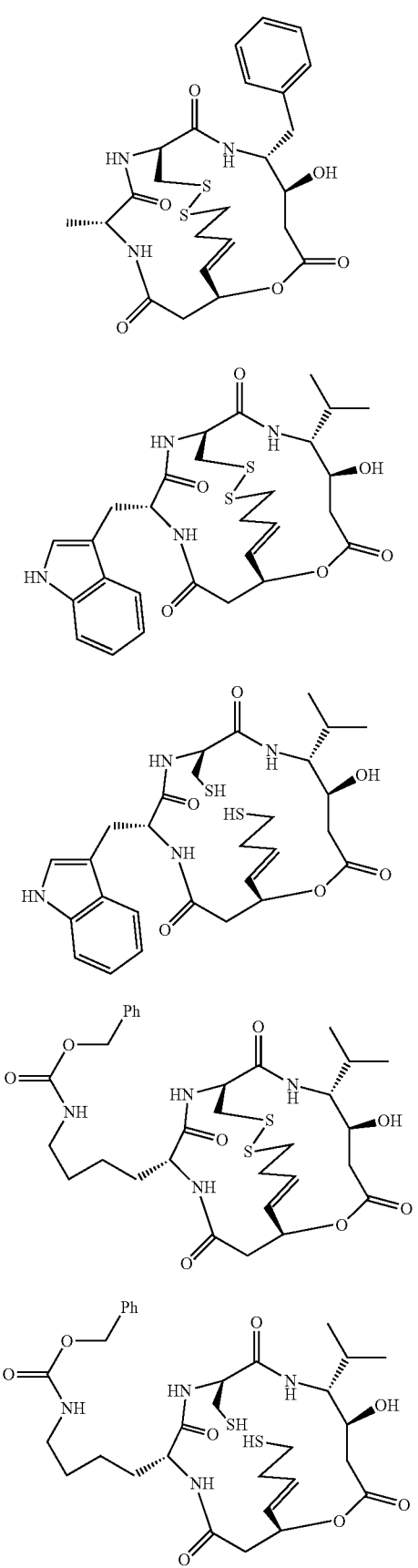
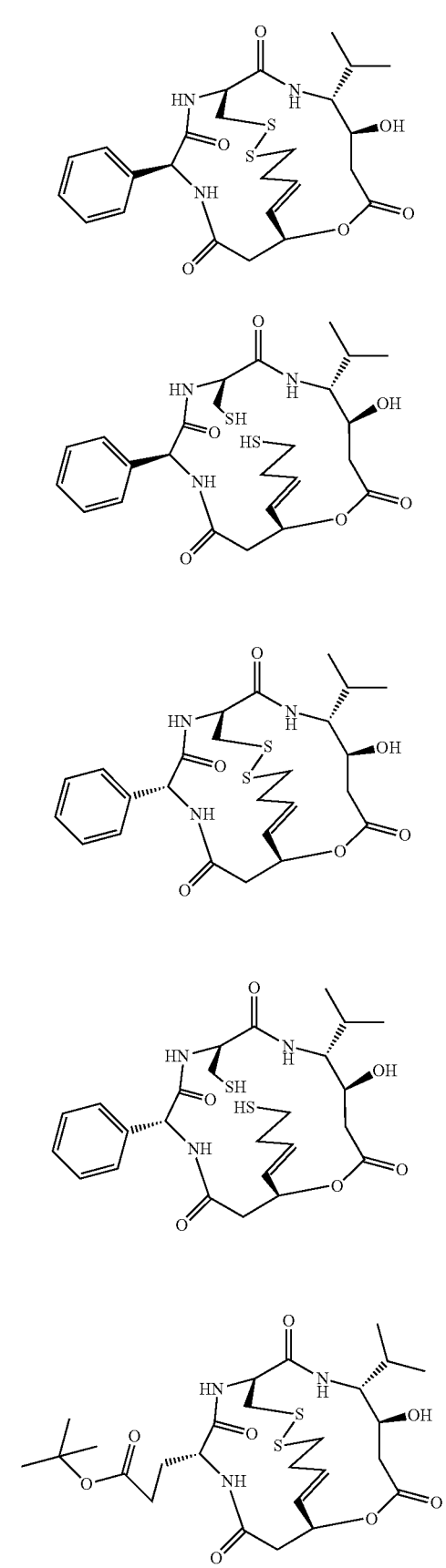

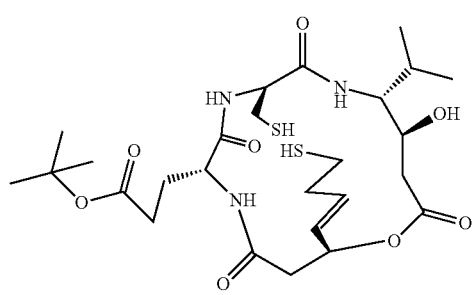
(10')
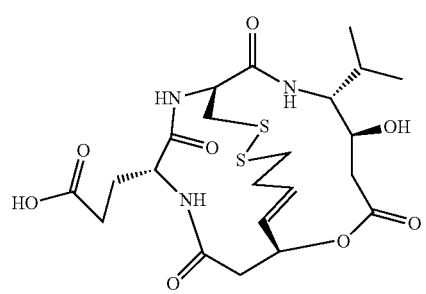
(11)
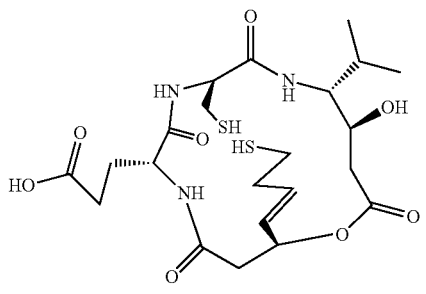
(11')
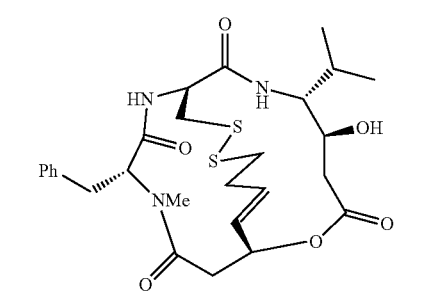
(12)
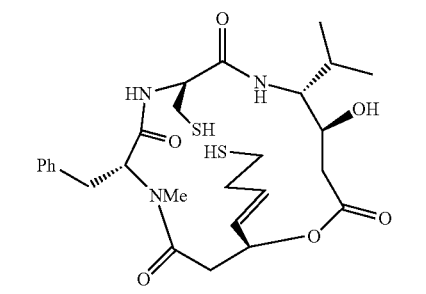
(12')
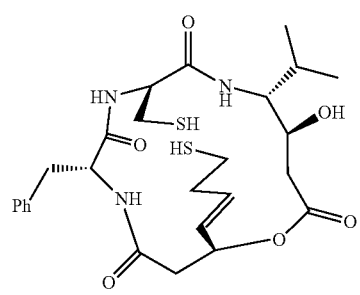
(14)
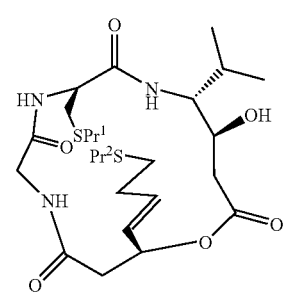
(13')
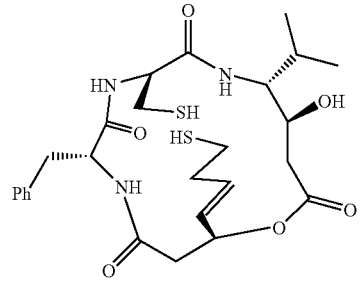
(14)
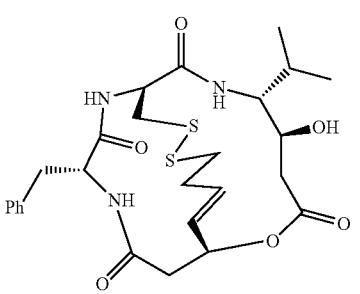
(14''')
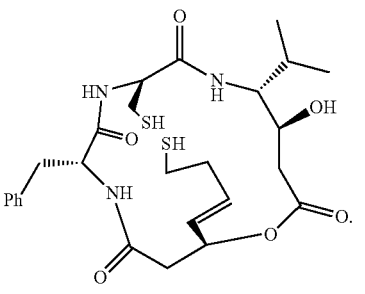
(14''''')

-continued

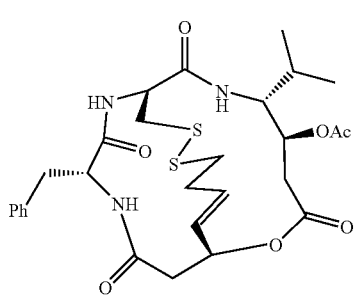

(14'''')

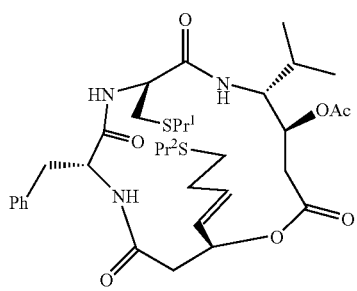

(14''''')

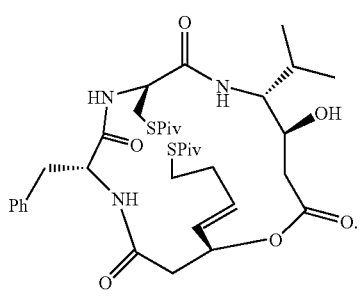

(14'''''')

13. A method for the treatment of a condition mediated by histone deacetylase (HDAC) wherein said method comprises administering, to a subject in need of such treatment, a compound of claim 1.

14. The method according to claim 13, wherein the condition is breast cancer, prostate cancer, ovarian cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes, osteoporosis, MDS, benign prostatic hyperplasia, endometriosis, oral leukopiakia, a genetically related metabolic disorder, an infection, Rubens-Taybi, fragile X syndrome, or alpha-1 antitrypsin deficiency.

15. The method according to claim 13, wherein the condition is cardiac hypertrophy, chronic heart failure or a skin inflammatory condition.

16. A method for accelerating wound healing, protecting hair follicles, or immunosuppression wherein said method comprises administering to a subject a compound of claim 1.

17. A pharmaceutical composition comprising a compound according to claim 1, and a pharmaceutically acceptable carrier or diluent.

18. The composition according to claim 17, which is in a form suitable for oral, rectal, parenteral, intranasal or transdermal administration or administration by inhalation or by suppository.

19. The composition according to claim 18, which is in the form of granules, a tablet, a capsule, a troche, a lozenge, an aqueous or oily suspension, or a dispersible powder.

20. The composition, according to claim 17, further comprising another inhibitor of HDAC, 21. The composition, according to claim 17, further comprising another chemotherapeutic or antineoplastic agent.

22. The analogue according to claim 1, wherein $R_3$ is selected from -L-O—C(O)—R', -L-C(O)—O—R", -L-A, -L-NR"R", -L-Het-C(O)-Het-R" and -L-Het- R".

23. A Spiruchostatin analogue of formula (14') or (1")

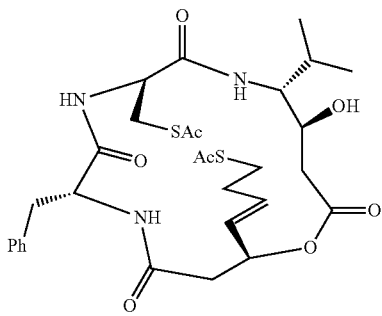

(14')

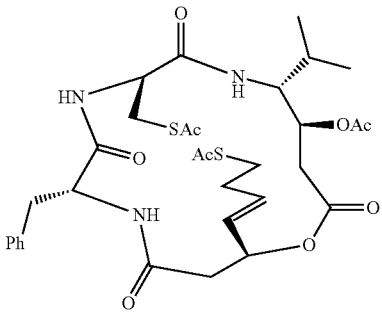

(14")

including isosteres and pharmaceutically acceptable salts thereof.

* * * * *

UNITED STATES PATENT AND TRADEMARK OFFICE
CERTIFICATE OF CORRECTION

PATENT NO. : 8,247,372 B2
APPLICATION NO. : 12/515880
DATED : August 21, 2012
INVENTOR(S) : Graham Keith Packham et al.

It is certified that error appears in the above-identified patent and that said Letters Patent is hereby corrected as shown below:

In the Specifications:

Column 48,
Lines 26-27, "$C_1,-C_4$" should read --$C_1-C_4$--

Column 48,
Line 28, "$C_1,-C_6$" should read --$C_1-C_6$--

Column 48,
Line 31, "$C_1,-C_4$" should read --$C_1-C_4$--

Column 48,
Line 38, "$C_1,-C_4$" should read --$C_1-C_4$--

In the Claims:

Column 49,
Claim 12,

"12. The analogue according to claim 1, which is a compound of formula (2), (2'), (3), (3'), (5'), (7), (7'), (8), (8'), (9), (9'), (9"), (9'''), (10), (10'), (11), (11'), (12), (12'), (14), (14'''), or (14'''')"

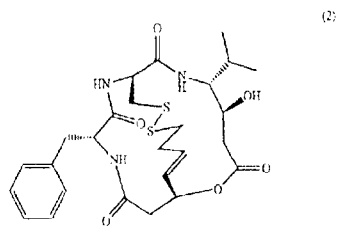

Signed and Sealed this
Twenty-eighth Day of May, 2013

Teresa Stanek Rea
*Acting Director of the United States Patent and Trademark Office*

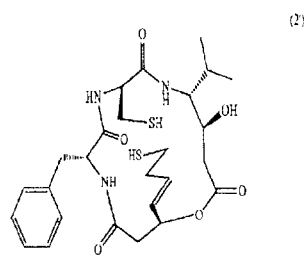
(2)
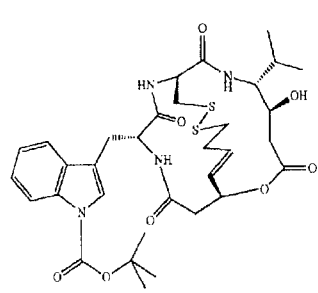
(3)
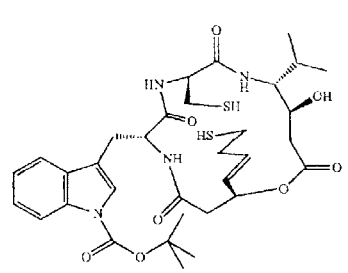
(3')
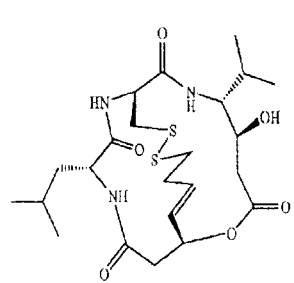
(4)

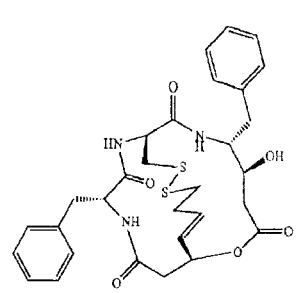
(5)
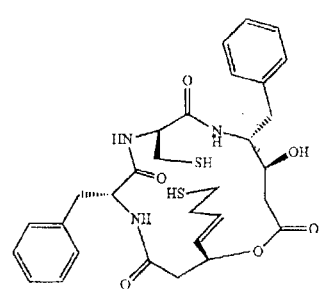
(5')
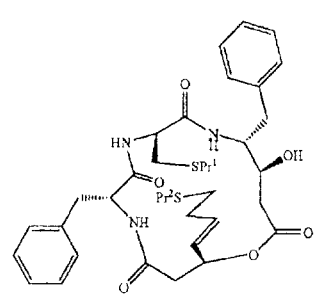
(5')
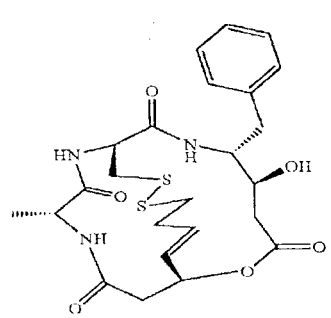
(6)

(7)
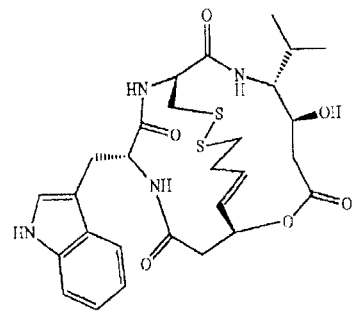
(7')
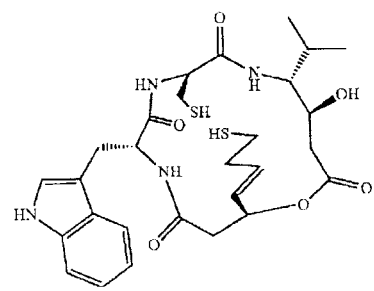
(8)
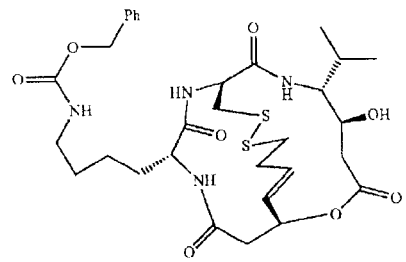
(8')
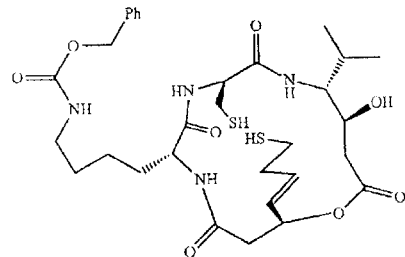

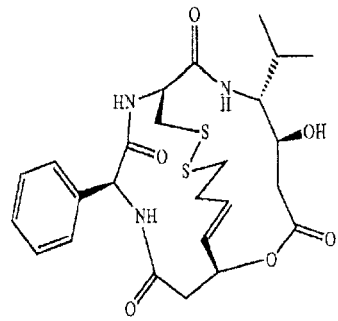
(9)
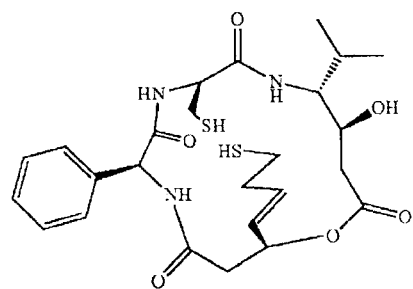
(9')
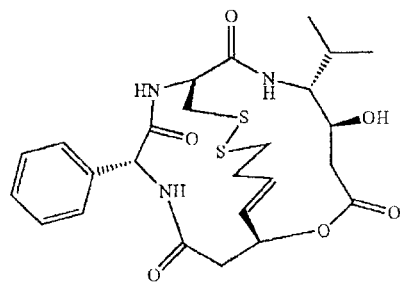
(9")
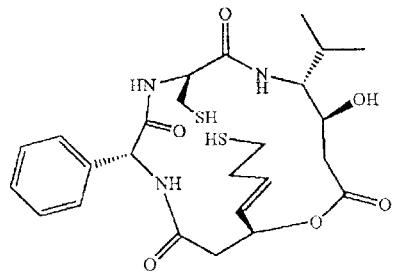
(9''')

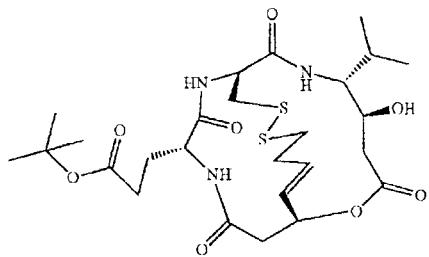
(10)
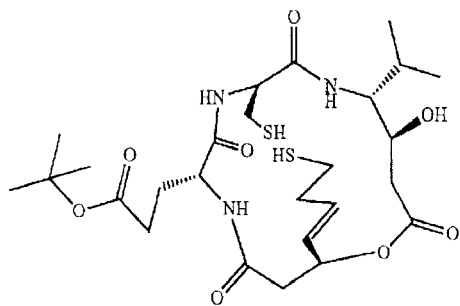
(10')
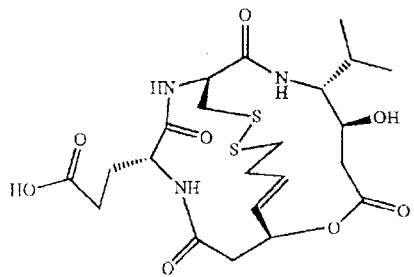
(11)
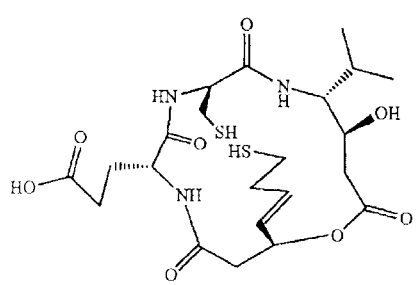
(11')

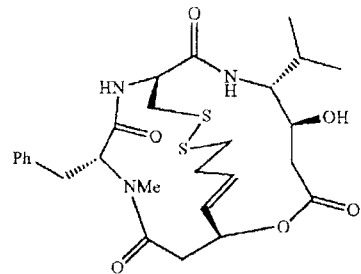
(12)
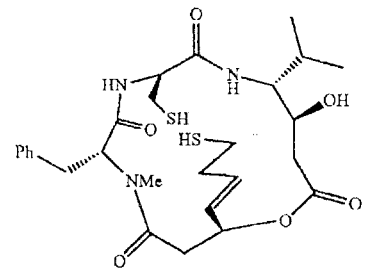
(12')
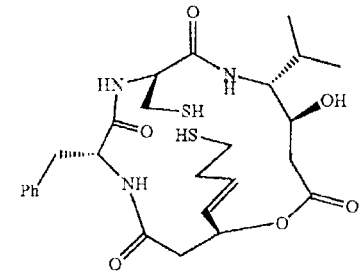
(14)
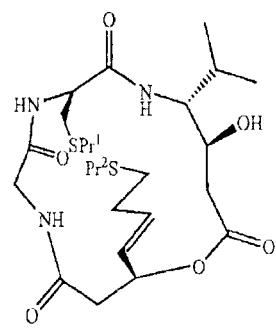
(13')

(14)
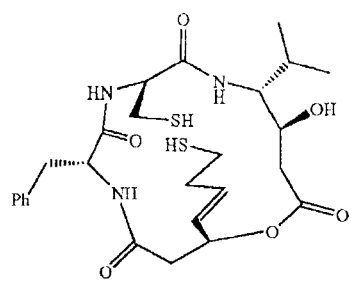
(14''')
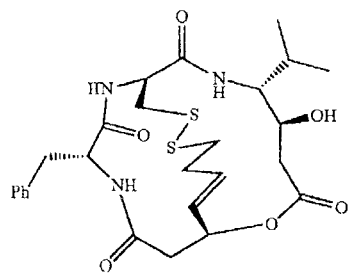
(14''''')
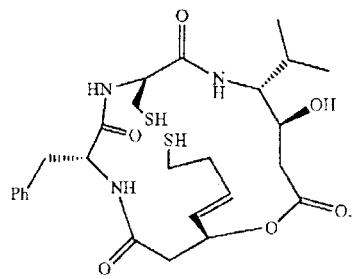
(14''')
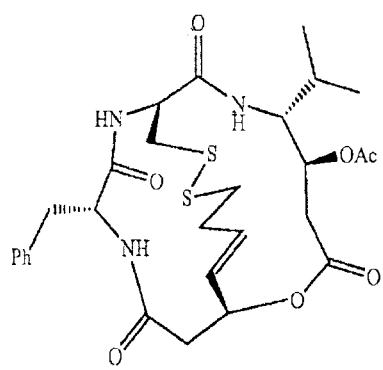

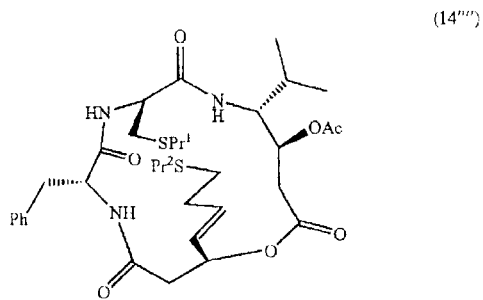
(14''')
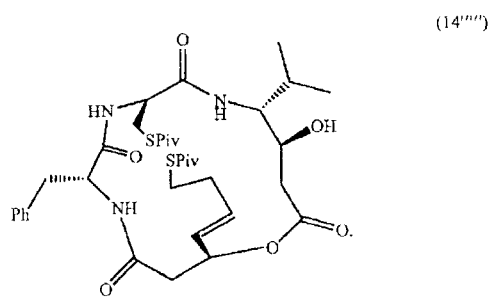
(14'''')
."
should read
--12. The analogue according to claim 1, which is a compound of formula (2), (2'), (3), (3'), (5), (5'), (7), (7'), (8), (8'), (9), (9'), (9"), (9'''), (10), (10'), (11), (11'), (12), (12'), (14), (14'''), or (14'''')
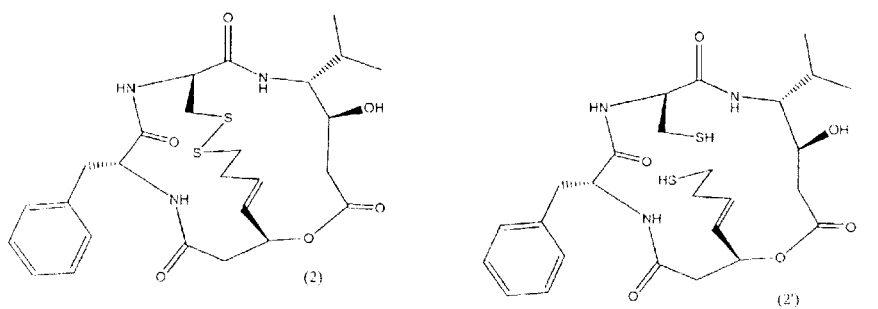

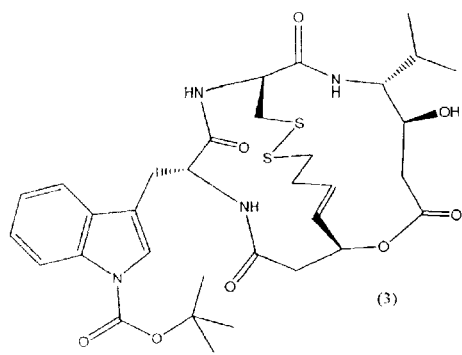
(3)
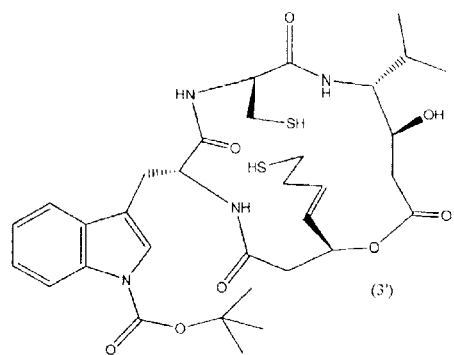
(3')
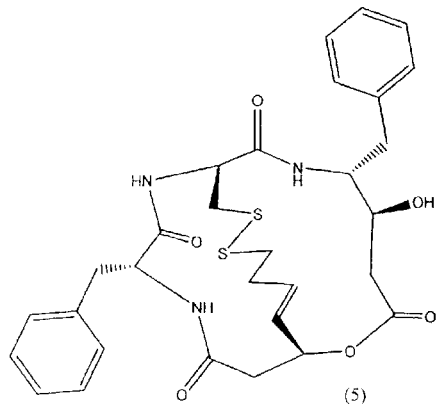
(5)
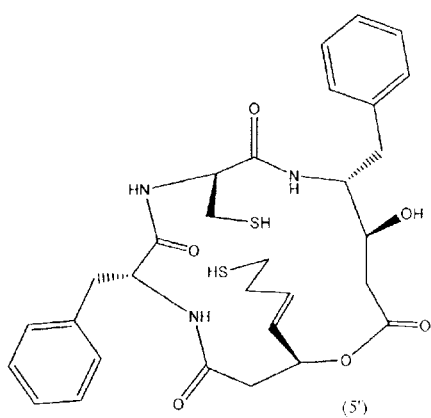
(5')
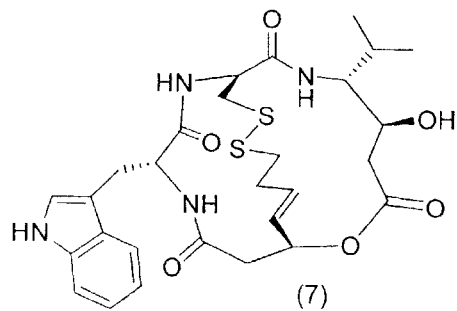
(7)
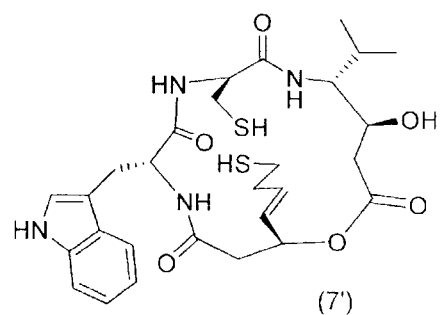
(7')

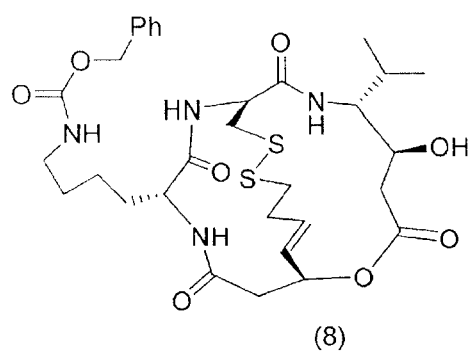
(8)
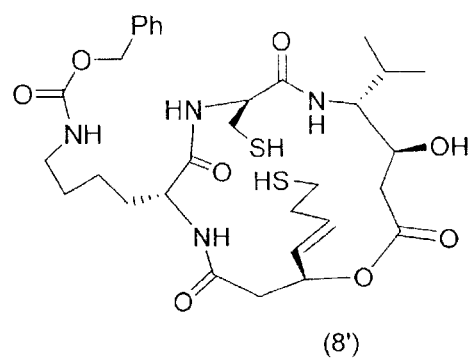
(8')
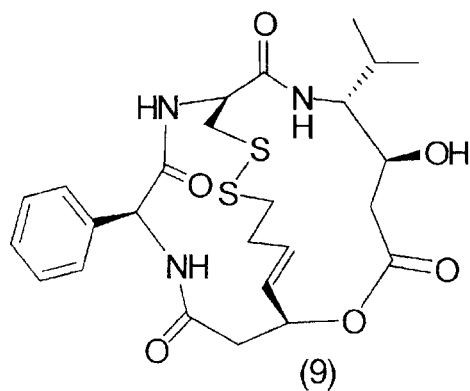
(9)
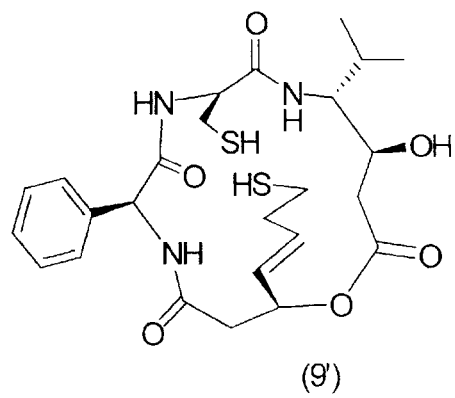
(9')
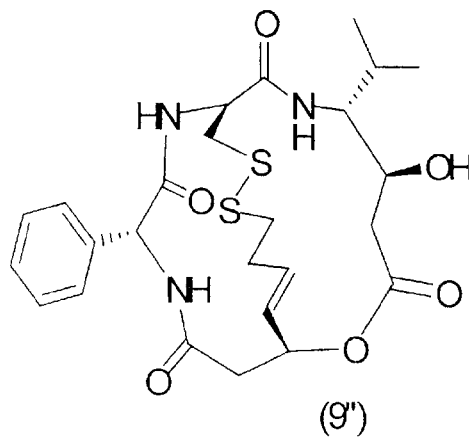
(9'')
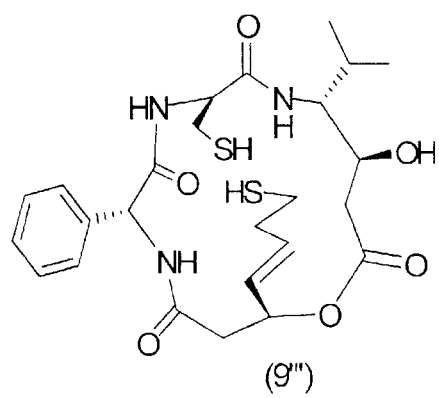
(9''')

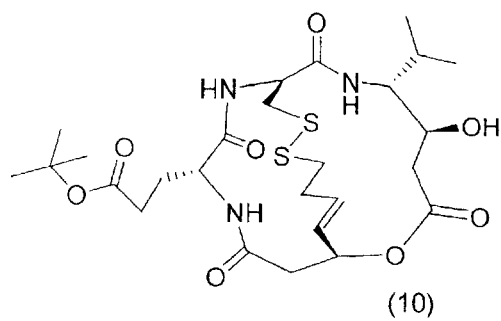
(10)
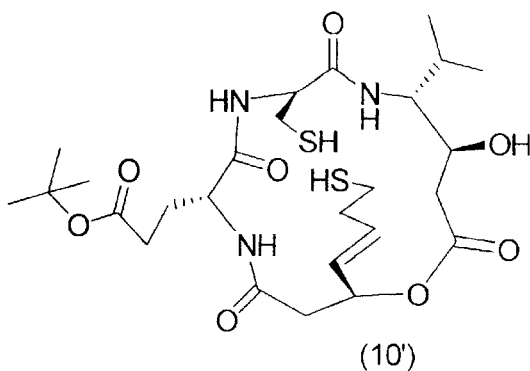
(10')
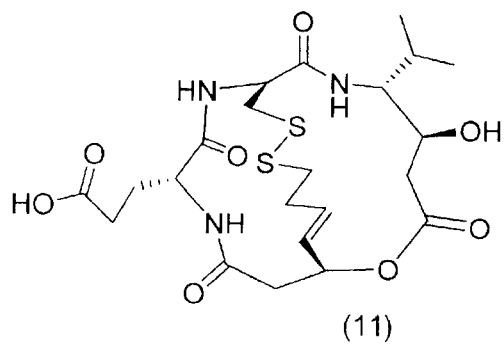
(11)
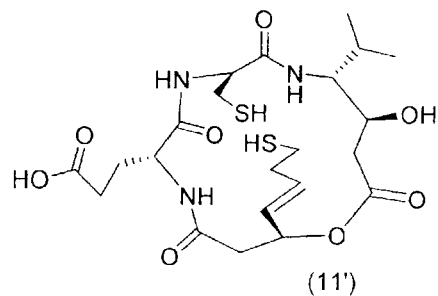
(11')
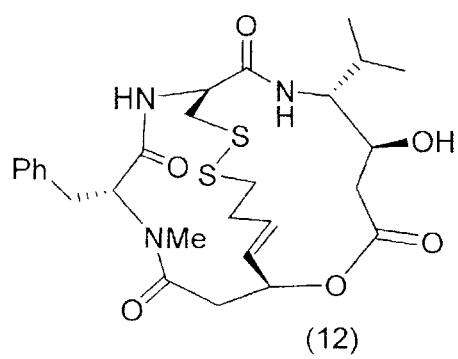
(12)
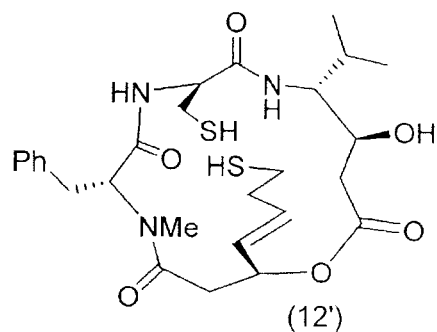
(12')

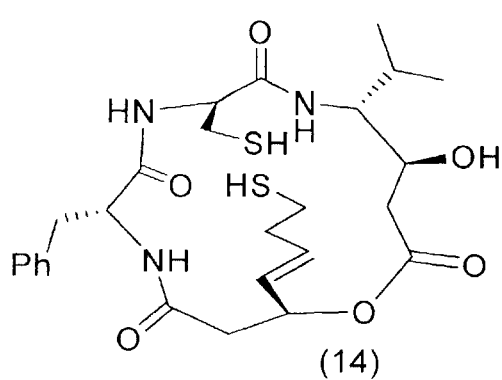
(14)
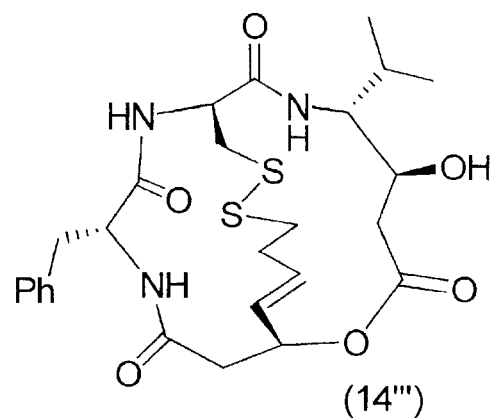
(14''')
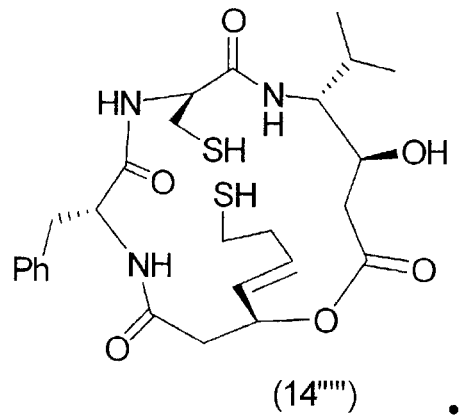
(14'''')
Column 56,
Line 21, "(1")" should read --(14")--